(12) United States Patent
Miller et al.

(10) Patent No.: US 8,410,070 B2
(45) Date of Patent: Apr. 2, 2013

(54) COMPOSITIONS AND METHODS FOR TREATING CANCER, INHIBITING PROLIFERATION, AND INDUCING CELL DEATH

(75) Inventors: Donald M. Miller, Louisville, KY (US); Shelia Diann Thomas, Louisville, KY (US); Kara Joyce Sedoris, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/063,509

(22) PCT Filed: Sep. 11, 2009

(86) PCT No.: PCT/US2009/056615
§ 371 (c)(1), (2), (4) Date: Apr. 29, 2011

(87) PCT Pub. No.: WO2010/030849
PCT Pub. Date: Mar. 18, 2010

(65) Prior Publication Data
US 2011/0213019 A1 Sep. 1, 2011

Related U.S. Application Data

(60) Provisional application No. 61/096,391, filed on Sep. 12, 2008.

(51) Int. Cl.
| | |
|---|---|
| *C12N 15/11* | (2006.01) |
| *A61K 48/00* | (2006.01) |
| *C07H 21/02* | (2006.01) |
| *C07H 21/04* | (2006.01) |

(52) U.S. Cl. .................. 514/44 A; 536/24.5
(58) Field of Classification Search ................ 536/24.1, 536/24.5; 514/44
See application file for complete search history.

(56) References Cited

U.S. PATENT DOCUMENTS

| 7,141,565 B1 * | 11/2006 | Whitten et al. ............ 514/229.5 |
| 7,314,926 B1 | 1/2008 | Miller et al. |
| 2004/0005601 A1 | 1/2004 | Siddiqui-Jain et al. |

* cited by examiner

*Primary Examiner* — Terra Cotta Gibbs
(74) *Attorney, Agent, or Firm* — Dinsmore & Shohl LLP

(57) ABSTRACT

Quadruplex-forming guanine-rich nucleic acid sequences are useful in compositions and methods for inhibiting cellular growth and proliferation and inducing cell death. Compositions for treating a patient are provided, including (i) a safe and effective amount of a sequence having at least 80% nucleic acid identity with a guanine-rich promoter gene oligonucleotide (GPGO), and (ii) a carrier, wherein the oligonucleotide forms at least one quadruplex.

18 Claims, 27 Drawing Sheets

A

BCL-2

β-Actin

B

BCL-2

SEQUENCE LISTING

```
<160> NUMBER OF SEQ ID NOS: 10

<210> SEQ ID NO 1
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Guanosine-rich promoter gene oligonucleotide
      sequence of c-myc

<400> SEQUENCE: 1
tggggagggt ggggagggtg gggaagg                                         27

<210> SEQ ID NO 2
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: Guanosine-rich promoter gene oligonucleotide
      sequence of c-Myb

<400> SEQUENCE: 2
ggaggaggag gtcacggagg aggaggagaa ggaggaggag ga                        42
```

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Guanosine-rich promoter gene oligonucleotide
      sequence of VEGF

<400> SEQUENCE: 3
ggggcgggcc gggggcgggg                                              20

<210> SEQ ID NO 4
<211> LENGTH: 32
<212> TYPE: DNA
<213> ORGANISM: Homo sapiens
<220> FEATURE:
<221> NAME/KEY: misc_feature
<222> LOCATION: (1)..(32)
<223> OTHER INFORMATION: Guanosine-rich promoter gene oligonucleotide
      sequence of K-ras

<400> SEQUENCE: 4
agggcggtgt gggaagaggg aagaggggga gg                                32

<210> SEQ ID NO 5
<211> LENGTH: 34
<212> TYPE: DNA
<213> ORGANISM: Homo sapiens
<220> FEATURE:
<221> NAME/KEY: misc_feature
<222> LOCATION: (1)..(34)
<223> OTHER INFORMATION: Guanosine-rich promoter gene oligonucleotide
      sequence of RET

<400> SEQUENCE: 5
agcgggtagg ggcggggcgg ggcggggggcg gtcc                             34

<210> SEQ ID NO 6
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Guanosine-rich promoter gene oligonucleotide
      sequence of HIF-1 alpha

<400> SEQUENCE: 6
ggggagggga gagggggcgg ga                                           22

<210> SEQ ID NO 7
<211> LENGTH: 48
<212> TYPE: DNA
<213> ORGANISM: Homo sapiens
<220> FEATURE:
<221> NAME/KEY: misc_feature
<222> LOCATION: (1)..(48)
<223> OTHER INFORMATION: Guanosine-rich promoter gene oligonucleotide
      sequence of PDGF-A

<400> SEQUENCE: 7
ggaggcgggg gggggggggc ggggcgggg gcggggagg ggcgcggc                 48

<210> SEQ ID NO 8
<211> LENGTH: 23
<212> TYPE: DNA

-continued

```
<213> ORGANISM: Homo sapiens
<220> FEATURE:
<221> NAME/KEY: misc_feature
<222> LOCATION: (1)..(23)
<223> OTHER INFORMATION: Guanosine-rich promoter gene oligonucleotide
      sequence of Bcl-2

<400> SEQUENCE: 8
gggcgcggga ggaaggggc ggg                                        23

<210> SEQ ID NO 9
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Guanosine-rich promoter gene oligonucleotide
      sequence of c-Kit

<400> SEQUENCE: 9
agggagggcg ctgggaggag gg                                        22

<210> SEQ ID NO 10
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Guanosine-rich promoter gene oligonucleotide
      sequence of RB

<400> SEQUENCE: 10 cgggggttt tgggcggc                                              18
```

US 8,410,070 B2

COMPOSITIONS AND METHODS FOR TREATING CANCER, INHIBITING PROLIFERATION, AND INDUCING CELL DEATH

RELATED APPLICATIONS

This application claims the benefit under 35 U.S.C. §119 (e) of U.S. Provisional Application No. 61/096,391, filed Sep. 12, 2008, and PCT/US09/056615, filed Sep. 11, 2009, which applications are hereby incorporated by reference in their entirety.

The presently disclosed invention and its respective embodiments were made with U.S. Government support under Grant No. DAMD17-98-1-8583, awarded by the U.S. Army Medical Research Development Command. The government has certain rights in this invention.

The present invention relates to the field of inhibiting cellular proliferation. More specifically, the present invention relates to methods and compositions for inhibiting cell proliferation and growth and inducing cell death comprising the administration of compositions comprising quadruplex-forming guanosine-rich promoter gene oligonucleotides (GPGOs) and their derivatives.

Guanine-rich nucleic acid sequences are capable of forming quadruplex, or four-stranded, conformations. These quadruplex structures are comprised of a series of quartets of hydrogen-bonded guanines, which together create a roughly cubical structure. Many cancer-related genes have quadruplex forming sequences in their G-rich promoter regions. These genes include, but are not limited to, the c-Myc, c-Myb, VEGF, RET, PDGF-A, Bcl-2, c-Kit, K-ras, Rb and HIF-1-α genes.

For example, the c-Myc quadruplex-forming sequence is located upstream of the P1 and P2 promoters of c-Myc, which are responsible for up to 95% of total c-myc transcription. This sequence is a 27 by guanine rich strand (Pu27) forming four loop isomers and appears to play an important role in regulating c-myc expression, although the exact mechanism is unknown. Cashman D J, et al., "Molecular modeling and biophysical analysis of the c-MYC NHE-III1 silencer element," *J. Mol. Model.* 2008;14:93-101.

Although these sequences are thought to play important regulatory roles in gene expression, the exact mechanism by which they regulate transcription is unclear. The inventors have previously shown that G-quadruplex forming oligonucleotides cause S-phase arrest in malignant cells, resulting in induction of cell death. The inventors have also previously shown that G-quadruplex forming oligonucleotides are remarkably stable with an intracellular half-life of greater than three weeks.

G-rich quadruplex forming genomic sequences provide an important target for methods and compositions that inhibit cell proliferation and induce cell death. The need exists to develop therapeutic methods and compositions comprising G-rich quadruplex forming oligonucleotides.

G-rich quadruplex forming oligonucleotides are useful in inhibiting cellular growth and proliferation, treating cancer, and inhibiting telomerase activity. Accordingly, it is an object of the present invention to provide a composition for treating a patient, comprising (i) a safe and effective amount of an oligonucleotide having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and (ii) a carrier, wherein the oligonucleotide forms at least one quadruplex.

In another embodiment, a composition for treating a patient is provided, comprising (i) a safe and effective amount of at least two oligonucleotides having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10, and (ii) a carrier, wherein each of said oligonucleotides forms at least one quadruplex.

In another embodiment, a composition for treating a patient is provided, comprising (i) a safe and effective amount of at least three oligonucleotides having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10, and (ii) a carrier, wherein each of said oligonucleotides forms at least one quadruplex.

In another embodiment, a method of treating cancer is provided, comprising administering to a patient in need thereof a composition comprising (i) a safe and effective amount of an oligonucleotide having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and (ii) a carrier, wherein the oligonucleotide forms at least one quadruplex.

In another embodiment, a method of inhibiting cell growth is provided, comprising contacting the cell with a composition comprising (i) a safe and effective amount of an oligonucleotide having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and (ii) a carrier, wherein the oligonucleotide forms at least one quadruplex.

In still another embodiment, a method of inhibiting telomerase activity of a cell is provided, comprising contacting the cell with a composition comprising (i) a safe and effective amount of an oligonucleotide having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and (ii) a carrier, wherein the oligonucleotide forms at least one quadruplex.

In another embodiment, a method of treating a patient having a tumor is provided, the method comprising (a) performing a biopsy of the patient's tumor; (b) determining a gene expression profile of the tumor; (c) identifying one or more genes that are overexpressed in the tumor, based on the gene expression profile of step (b); (d) selecting one or more GPGO sequences corresponding to the overexpressed genes identified in step (c); (e) administering to the patient a composition comprising a safe and effective amount of the one or more GPGO sequences of step (d).

These and other objects, features, embodiments, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

FIGS. 1-6 show results from circular dichroism spectroscopy of several GPGOs (G-rich promoter sequences of PU27, VEGF, BCL-2, KRAS, HIF-1-α, RB). Note absorbance at 260 nm, indicative of quadruplex formation, compared to the mutant sequences which did not form quadruplexes. Absorbance at or near 260 nm may be used to determine if a potential GPGO forms a quadruplex.

FIG. 7 shows changes in cell proliferation of U937 leukemia cells after addition of 5 µM or 10 µM of GPGOs (KRAS, BCL-2, HIF-1-α, RB, PU27, VEGF) at 72 h as determined by MTT assay. Bars represent the mean±SEM of the percent change from untreated U937 cells. G-rich promoter sequences exhibit dose-dependent inhibition of cell proliferation of U937 cells.

FIG. 8 shows cell cycle analysis of U937 cells after 6-72 h of treatment with 10 µM PU27 as determined by flow cytometry. An increase in G1-arrest was measured beginning at 24 h.

FIG. 9 shows cell analysis comparing several GPGOs (PU27, VEGF, BCL-2, KRAS, RB) as determined by flow cytometry. An increase in G1-arrest was observed in U937 cells treated with PU27 while an increase in S-phase arrest was measured with the KRAS promoter sequence, genes both directly involved in the regulation of cell proliferation. No significant changes occurred with the VEGF, BCL-2, or RB promoter sequences.

FIGS. 10 and 11 show uptake of fluorescein-labeled PU27 (a GPGO) or Mut PU27 (not a GPGO) (10 µM) in U937 cells after 1 and 72 h as determined by flow cytometry. Greater uptake of PU27 into cells immediately after 1 h and after 72 h of incubation was observed, compared to Mut PU27.

FIG. 12 shows uptake of fluorescein-labeled PU27 or MutPU27 (10 µM) after 6-72 h by Amnis Image Stream Analysis. Fixed cells were stained with the DRAQ nuclear stain (pink). A significant increase in PU27 uptake (green) and nuclear translocation (yellow) was measured compared to MutPU27.

FIGS. 13 and 14 show serum and intracellular (S100) stability of the PU27 (a GPGO) and Mut PU27. PU27 and Mut PU27 sequences were $^{32}$P labeled and incubated in RPMI media with 10% FBS at 37° C. or in the presence of U937 S100 extract at 37° C. for 0-72 h. PU27 showed greater intracellular and serum stability from 24-72 h compared to Mut PU27.

FIG. 15 shows the time course of changes in c-Myc mRNA from 6-72 h in response to the c-Myc quadruplex promoter sequence PU27 (10 µM). PU27 decreased c-myc myc mRNA by over 90% after 72 h. No significant change occurred in response to MutPU27.

FIG. 16 show RT-PCR analysis of c-Myc, RB, KRAS, BCL-2, HIF-1, VEGF, ENOL, and Glut-1 gene expression after 72 h treatment with PU27. Bars represent the expression ratio of gene expression compared to untreated U937 cells (Unt). PU27 treatment most dramatically affects c-myc expression suggesting targeting of c-myc transcription.

FIG. 17 shows the time course of c-Myc expression in response to PU27 or MutPU27 by Western blot analysis. β-actin was used as the loading control. PU27 significantly decreased c-Myc protein expression compared to MutPU27.

FIG. 18 shows the change in c-Myc promoter activity in response to PU27. U937 cells were transiently transfected with a c-Myc promoter construct expressing firefly luciferase (h-myc) and treated with 10 µM PU27 or MutPU27 for 24 h. The Renilla control plasmid was used to standardize for transfection efficiency. Note 70% inhibition of c-Myc promoter activity with PU27 compared to MutPU27.

FIG. 19 shows inhibition of telomerase activity of U937 cells after treatment with GPGOs (PU27, BCL-2, HIF-1) for 72 h. Bars represent mean±SEM. Note dose-dependent inhibition of telomerase activity.

FIG. 20 shows changes in cell proliferation of U937 leukemia cells after 3 days (A) and 6 days (B) in response to dose escalation of the c-Myc quadruplex promoter sequence (PU27) as determined by MTT assay. Bars represent mean±SEM of the percent change from untreated U937 cells. Note dose-dependent inhibition of cell proliferation of U937 cells in response to PU27 (IC50<3 µM), but not MutPU27. In panel C, after U937 cells were treated for 96 h with PU27 or MutPU27 (10 µM), they were washed, counted, and replated (equal cell number) and grown for 6 days. Changes in cell growth were determined by MTT assay. Bars represent mean±SEM. Note an absence of cells in response to PU27 indicating that the antiproliferative effect of PU27 after 96 h is irreversible.

FIGS. 21-29 show changes in cell proliferation of various cell lines in response to G-rich quadruplex-promoter sequences after 6 days as determined by MTT assay: FIG. 21: HL60 cells, promeyelocytic leukemia; FIG. 22: A549 cells, lung cancer (alveolar basal epithelial cells); FIG. 23: SK-BR-3 cells, breast cancer; FIG. 24: DU145 cells, prostate cancer; FIG. 25: MDA-MB-231 cells, breast cancer; FIG. 26: LnCAP cells, prostate cancer; FIG. 27: H1299 cells, lung cancer; FIG. 28: Raji cells, Burkitt's lymphoma; FIG. 29: Me1-28 cells, melanoma.

Figure 32:
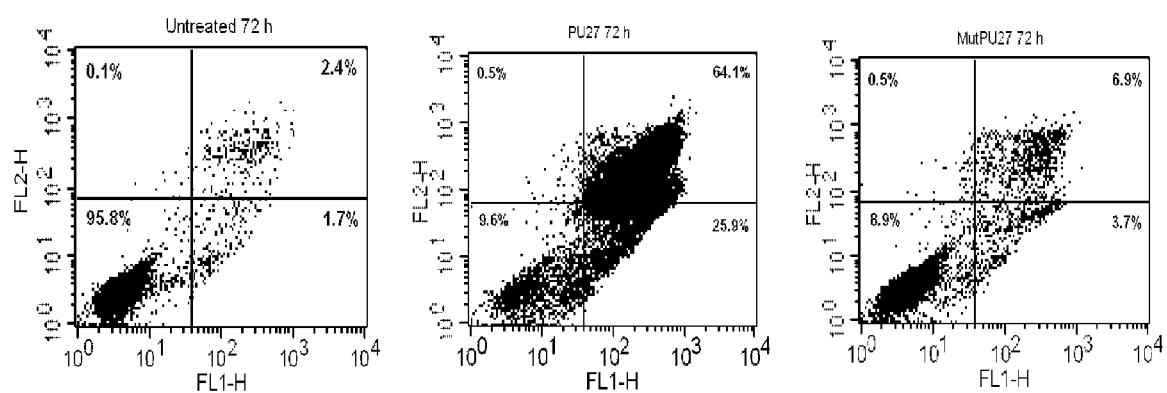

FIG. 32 shows annexin (FL1-H) and propidium iodide (PI,FL2-H) staining of untreated cells or cells treated with 10 µM PU27 or MutPU27 after 72 h. Note a significant increase (25.9%) in annexin positive only cells (lower right quadrant) and PI and annexin positive cells (64.1%, upper right quadrant) with PU27 treatment. Cells staining annexin positive only are indicative of early stage apoptosis while uptake of PI into cells, in which viable cells are normally impermeable, is indicative of dead cells.

Figure 33:
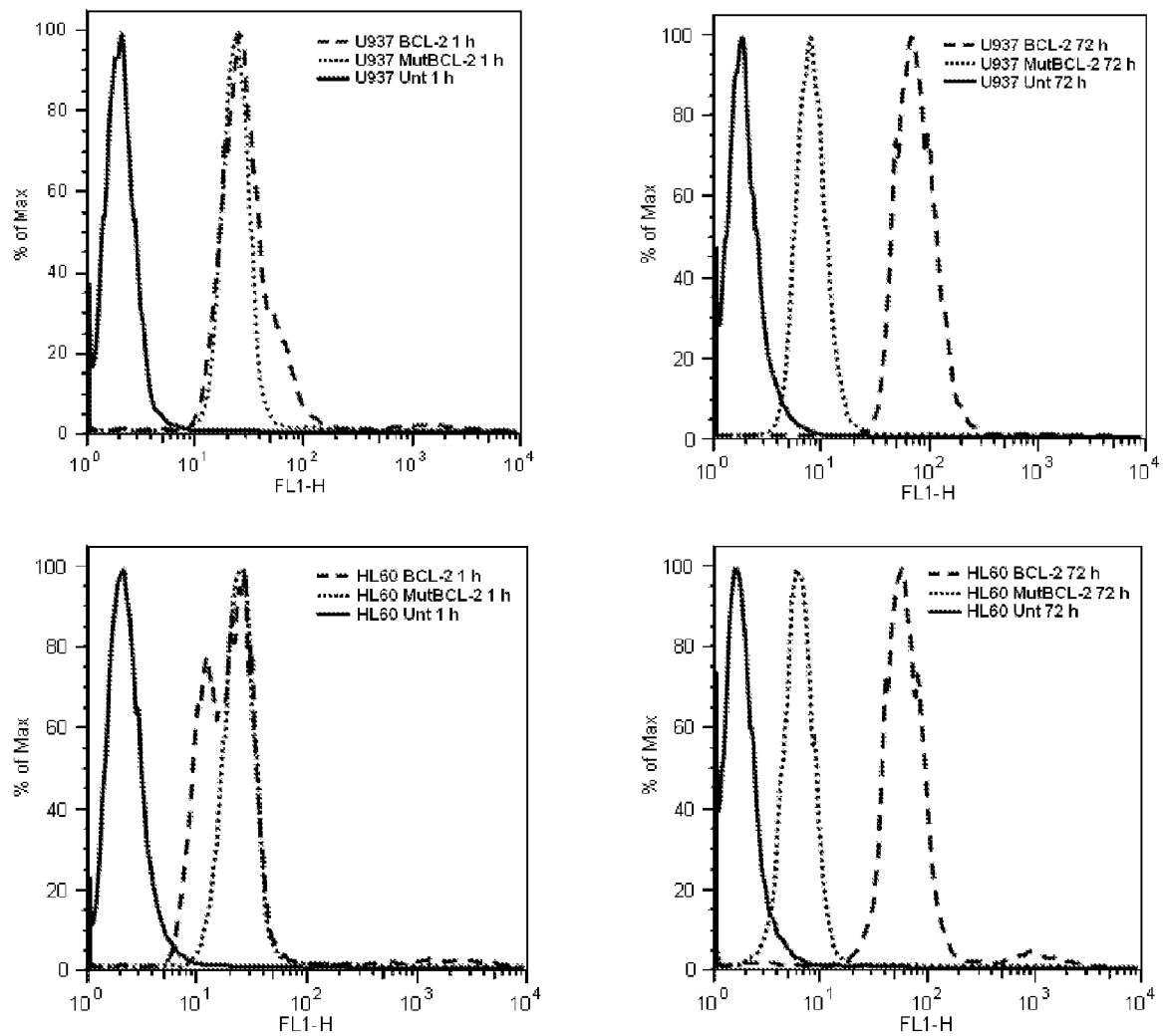

FIG. 33 shows uptake of fluorescein-labeled BCL-2 (a GPGO) or MutBCL-2 (not a GPGO) (10 µM) in U937 and HL60 cells after 1 and 72 h as determined by flow cytometry. Greater uptake of BCL-2 into cells was measured after 72 h compared to MutBCL-2.

Figure 1:
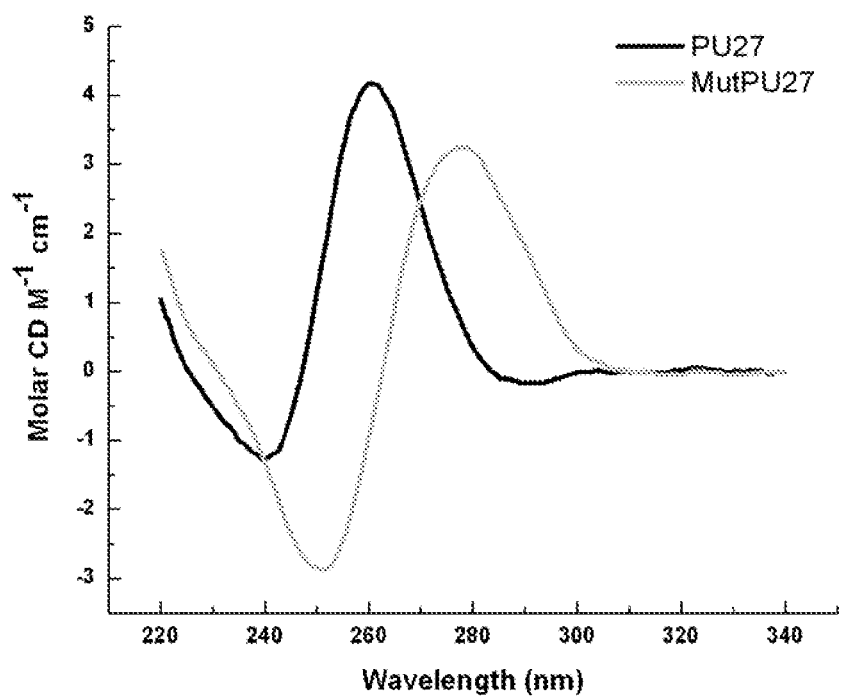
Figure 2:
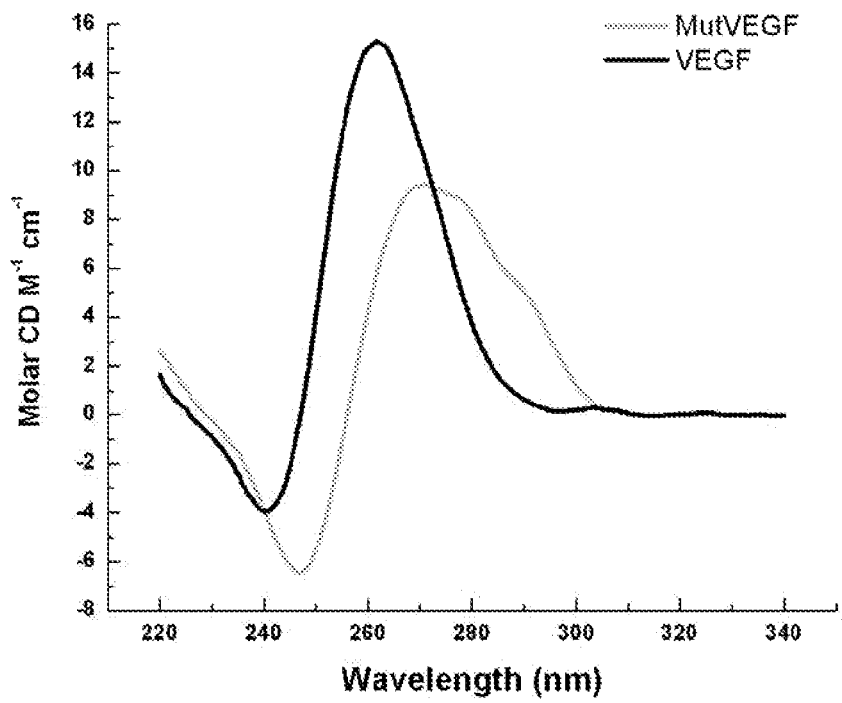
Figure 3:
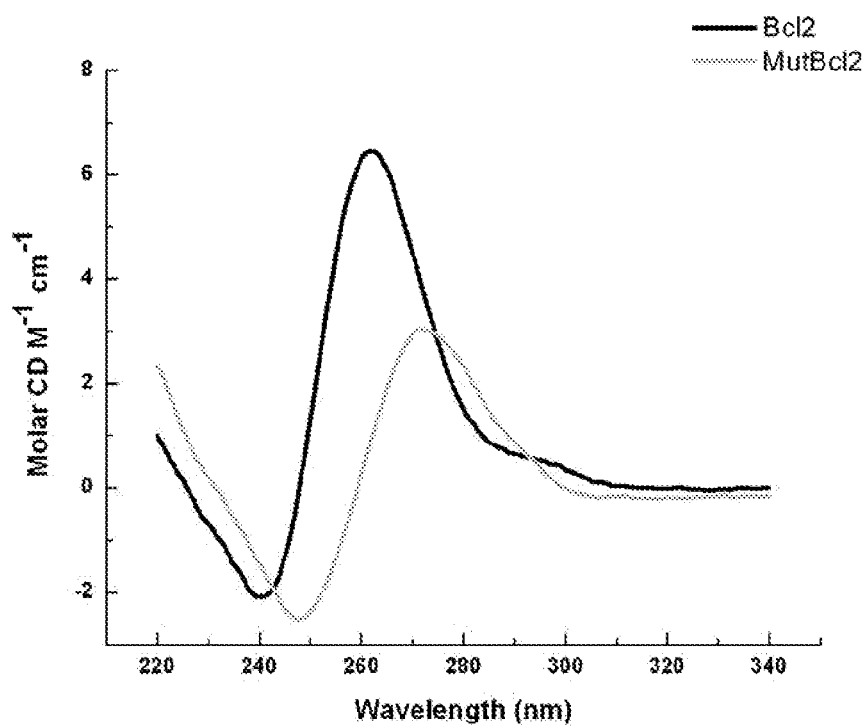
Figure 4:
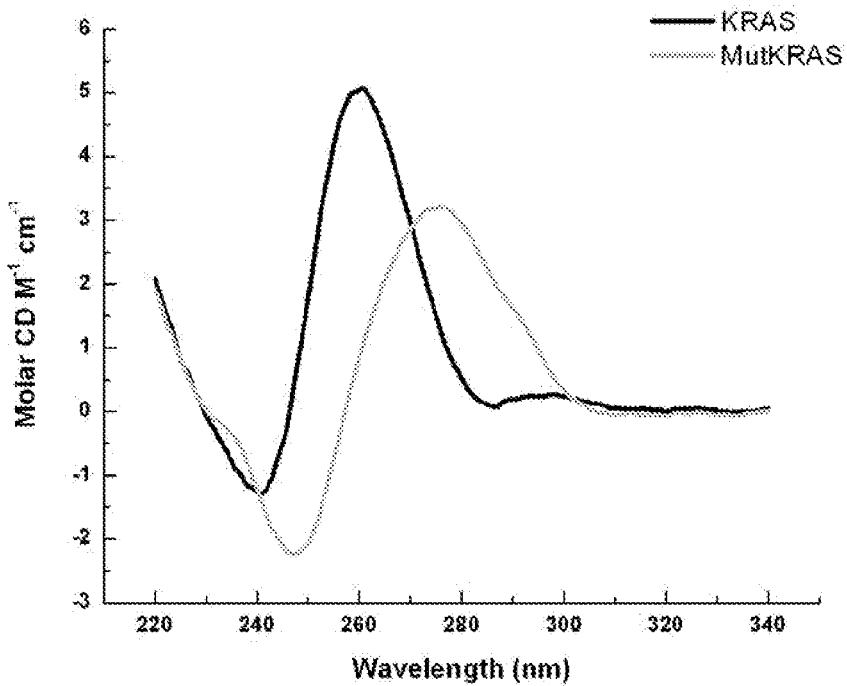
Figure 5:
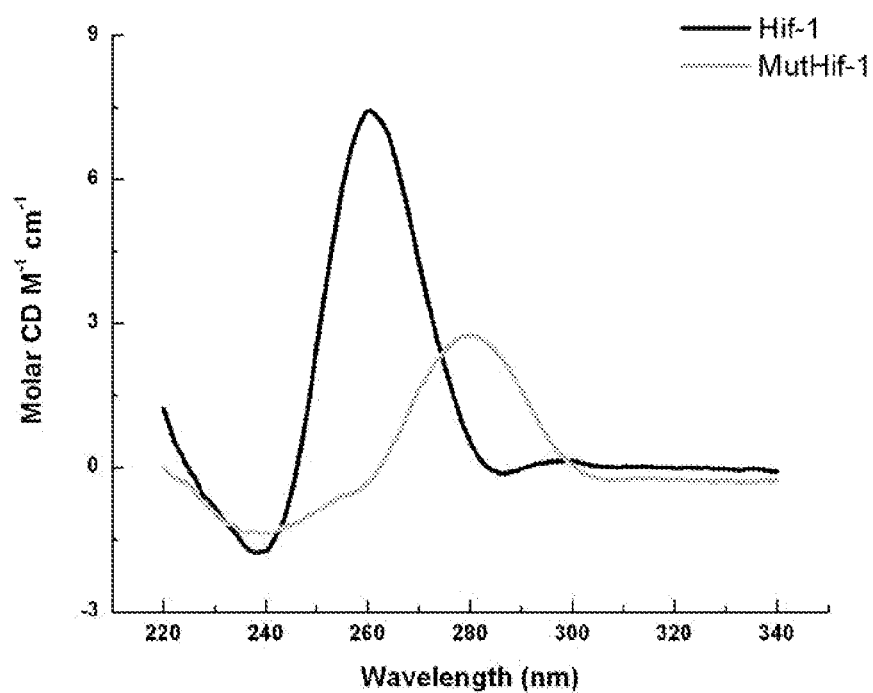
Figure 6:
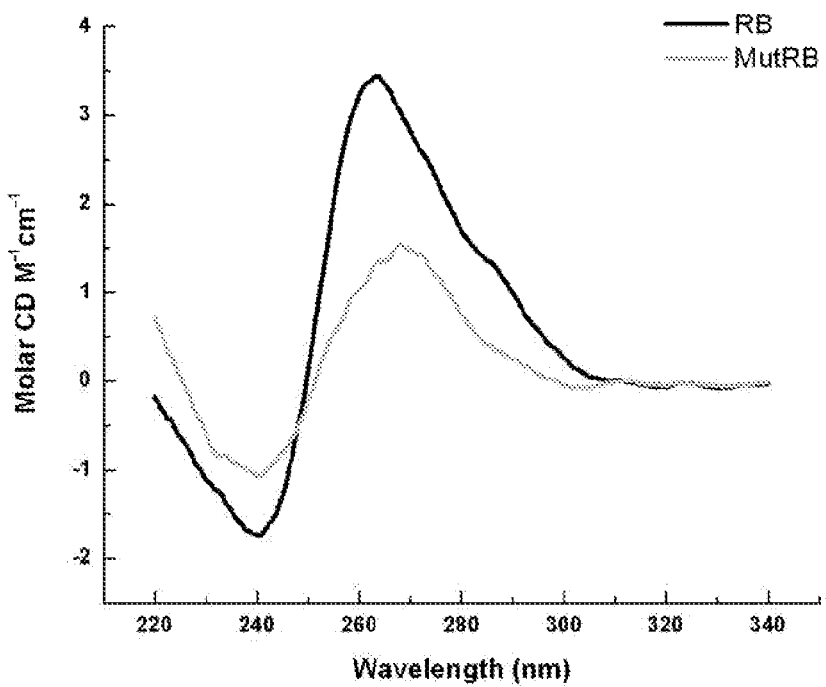
Figure 7:
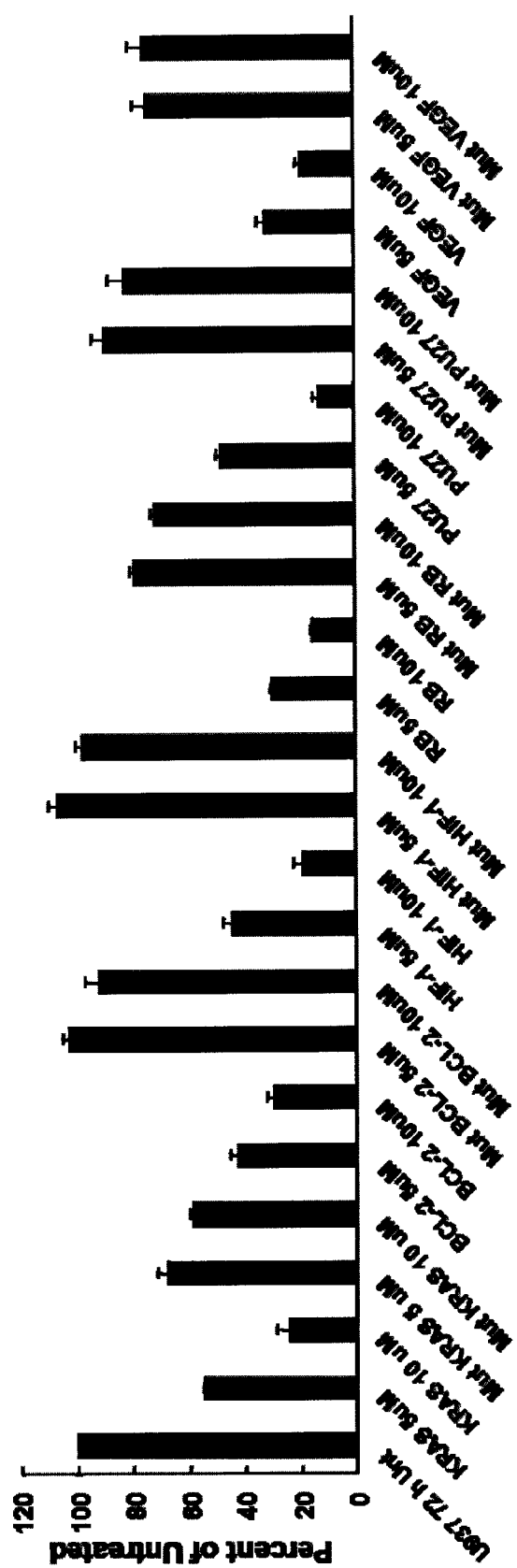
Figure 8:
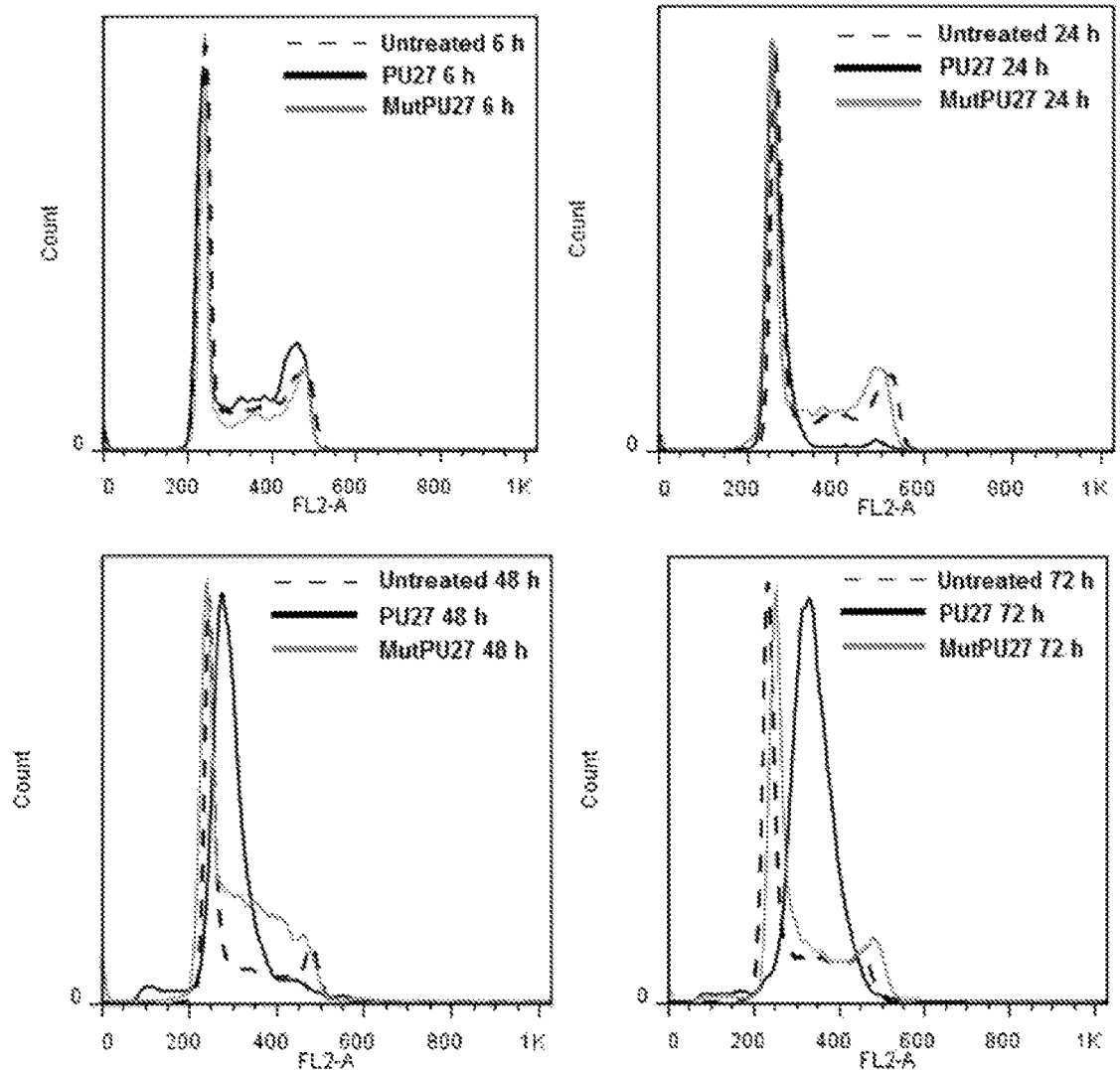
Figure 9:
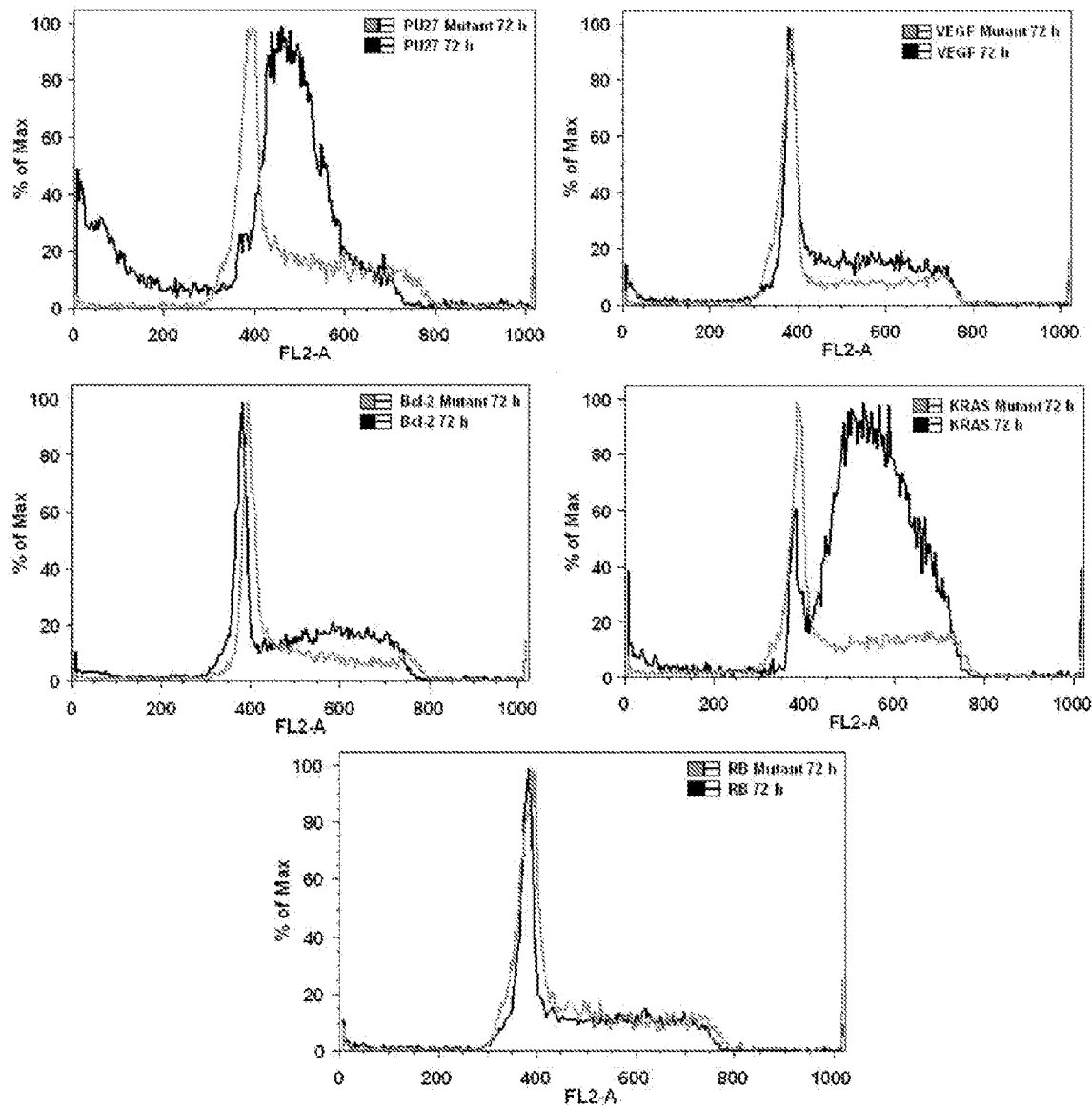
Figure 10:
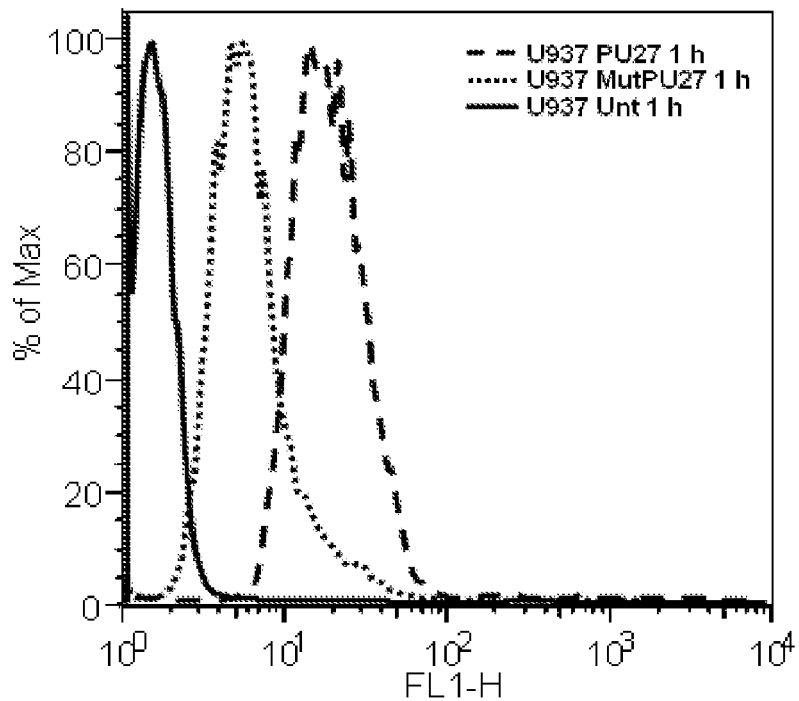
Figure 11:
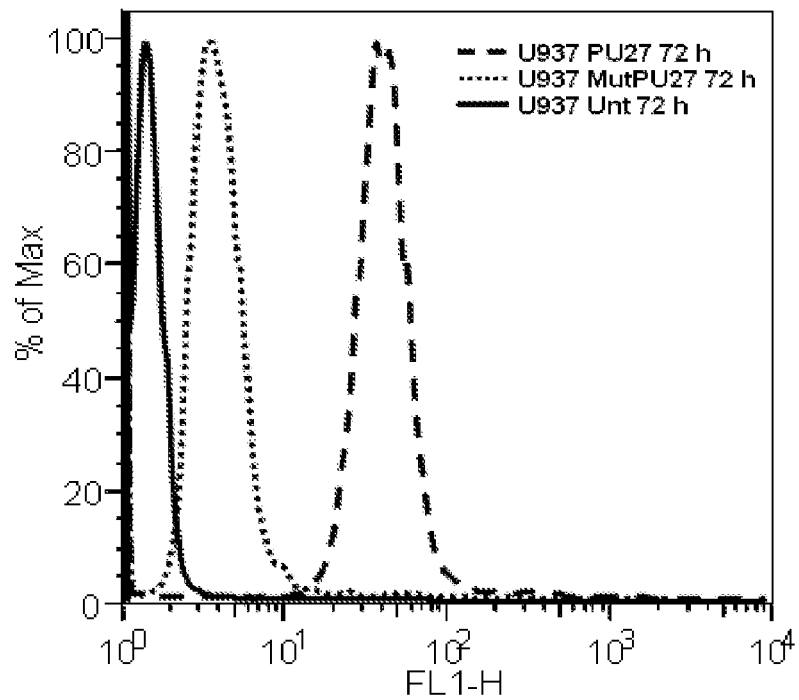
Figure 12:
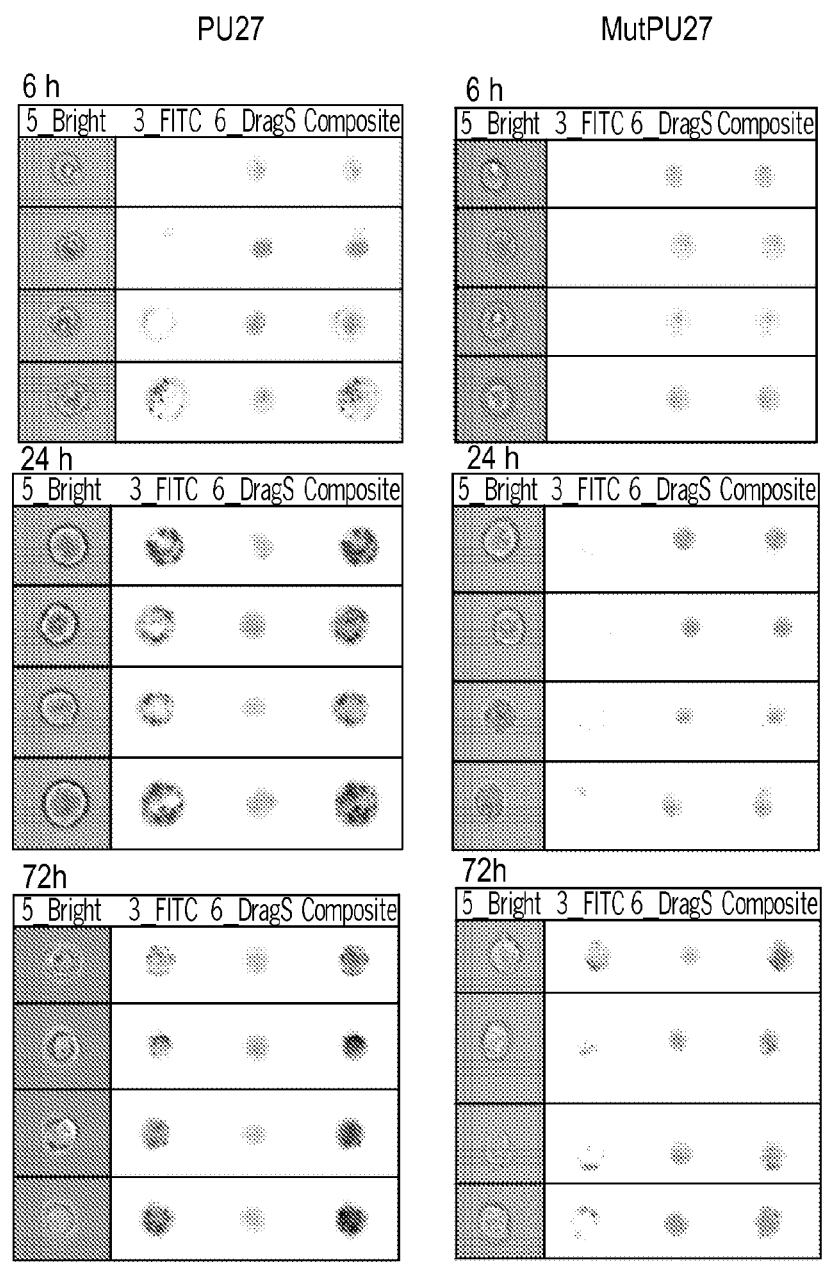
Figure 13:
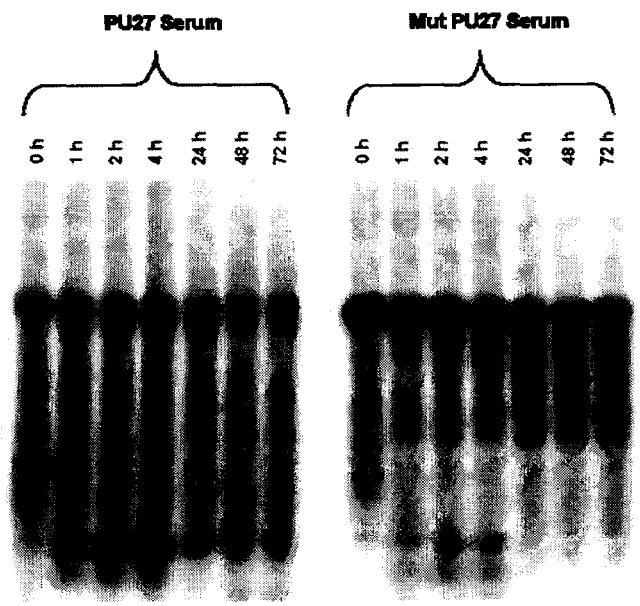
Figure 14:
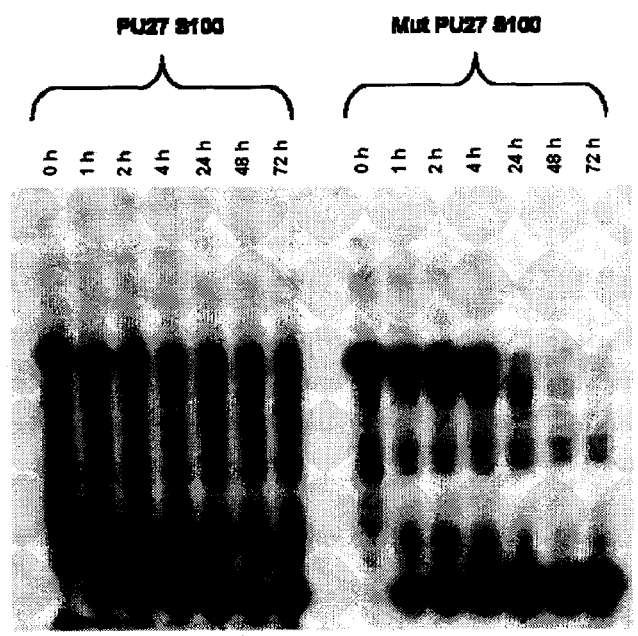
Figure 15:
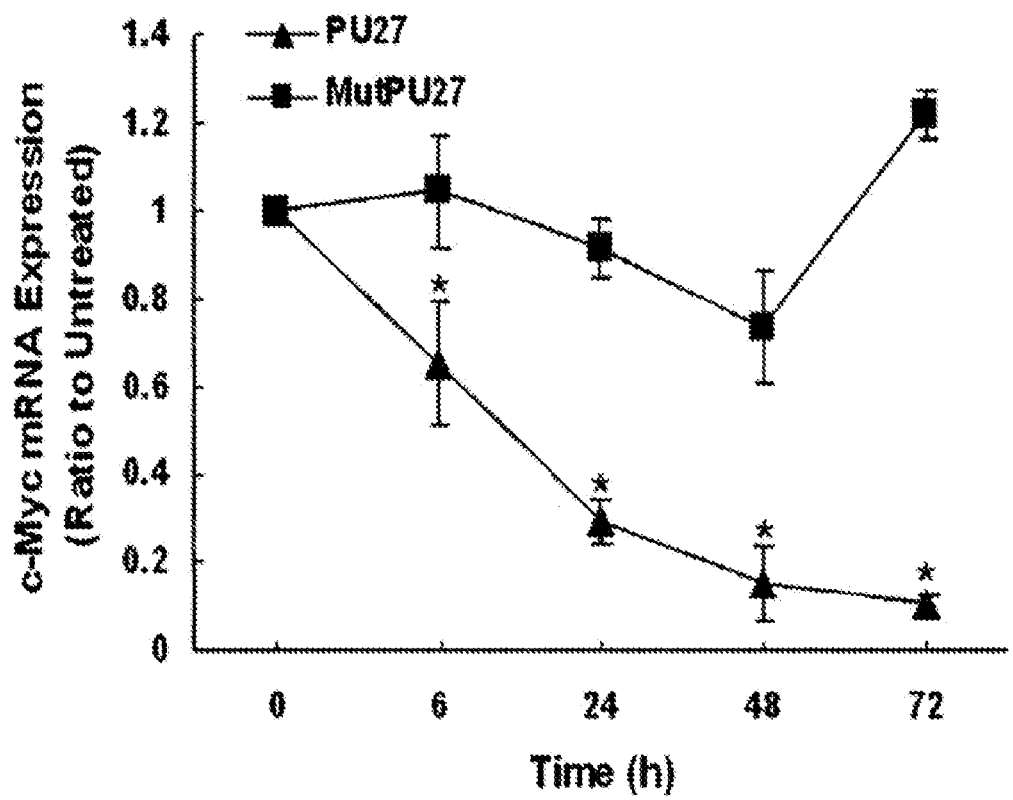
Figure 16:
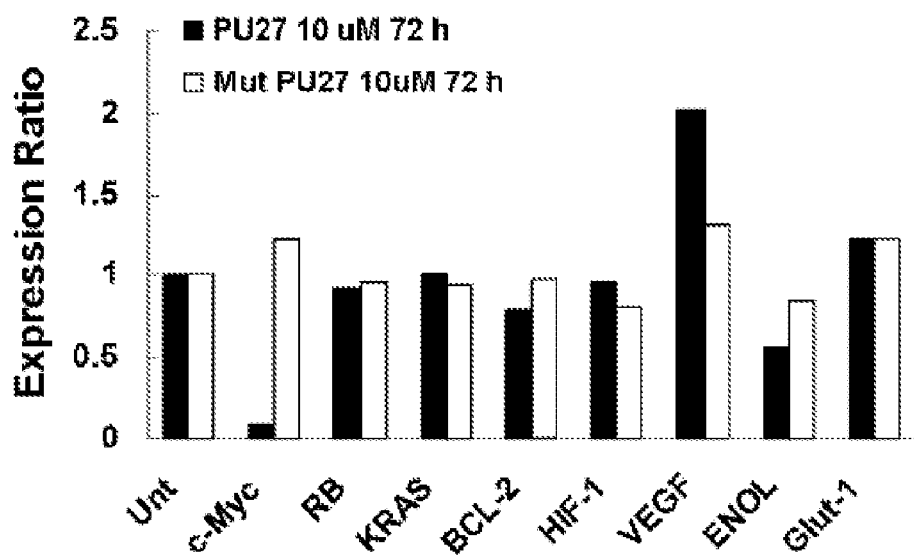
Figure 17:
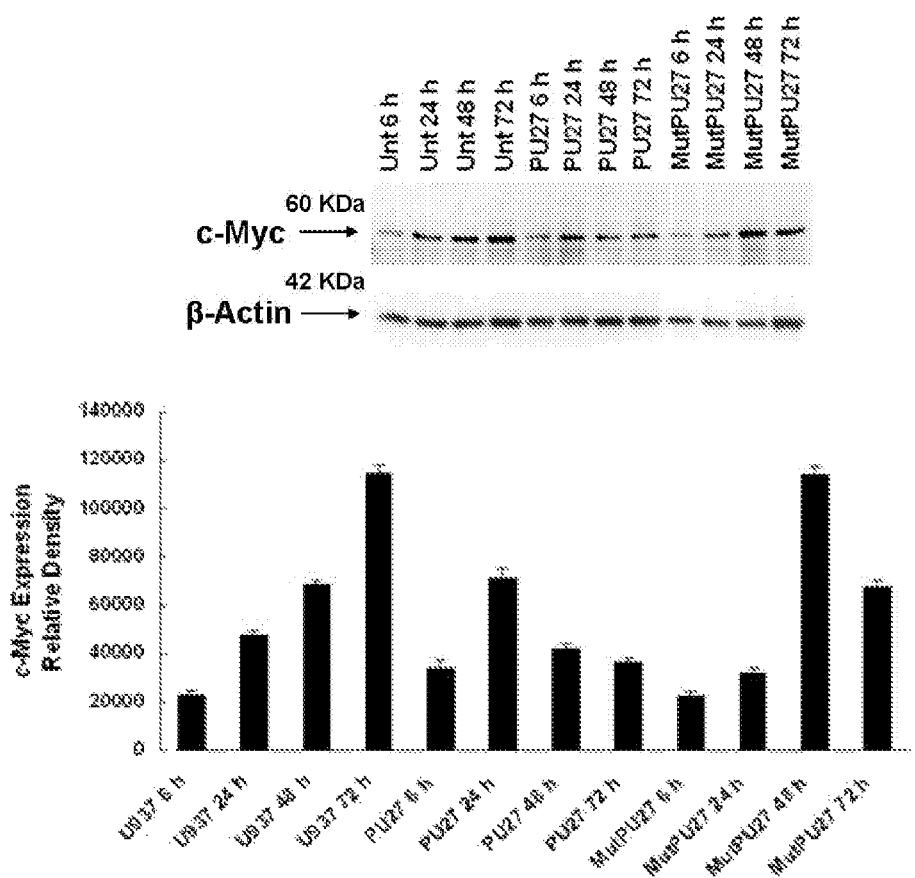
Figure 18:
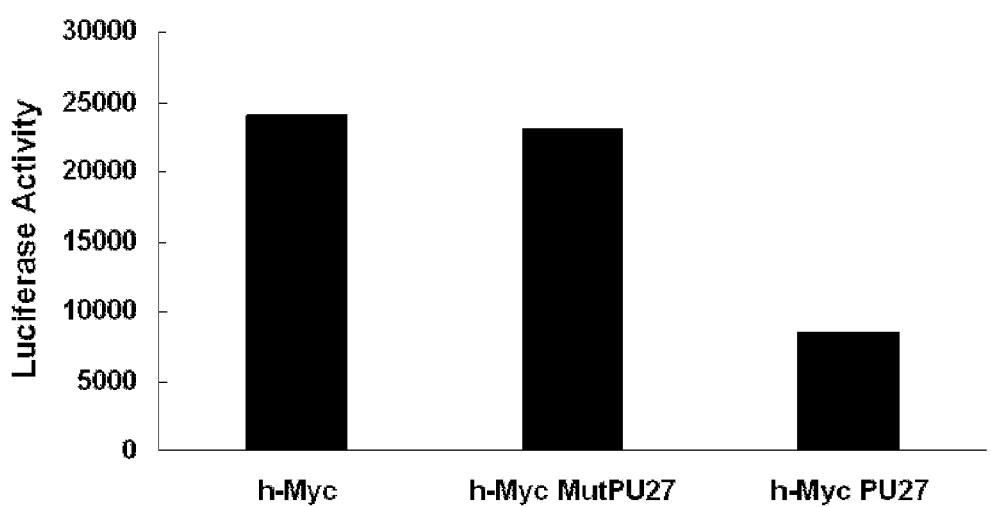
Figure 19:
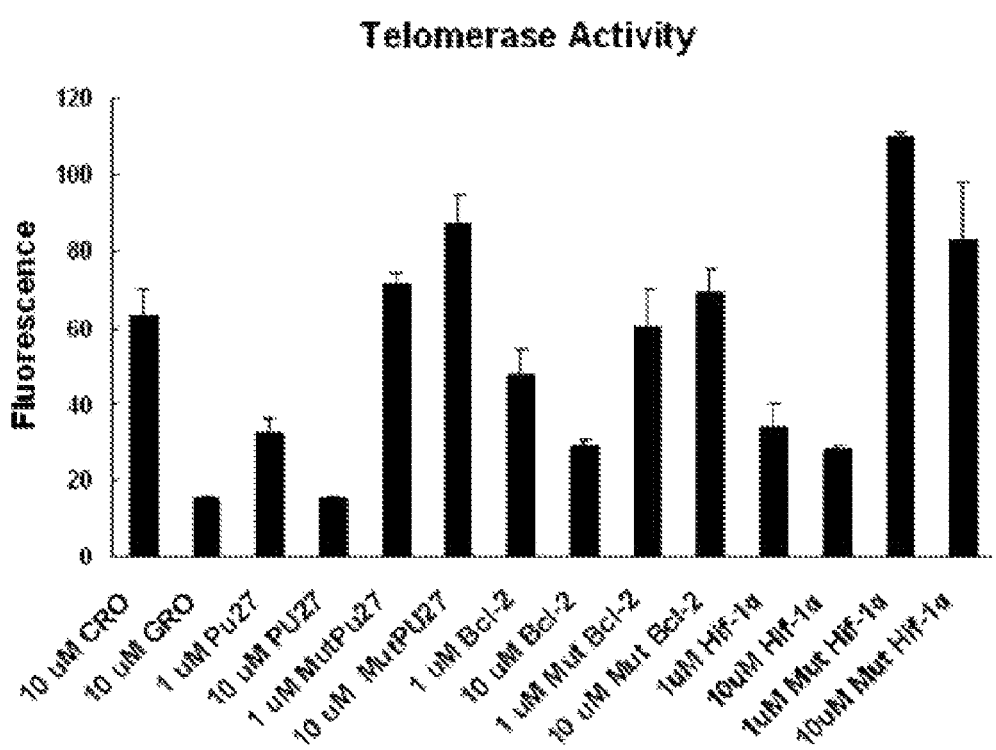
Figure 20:
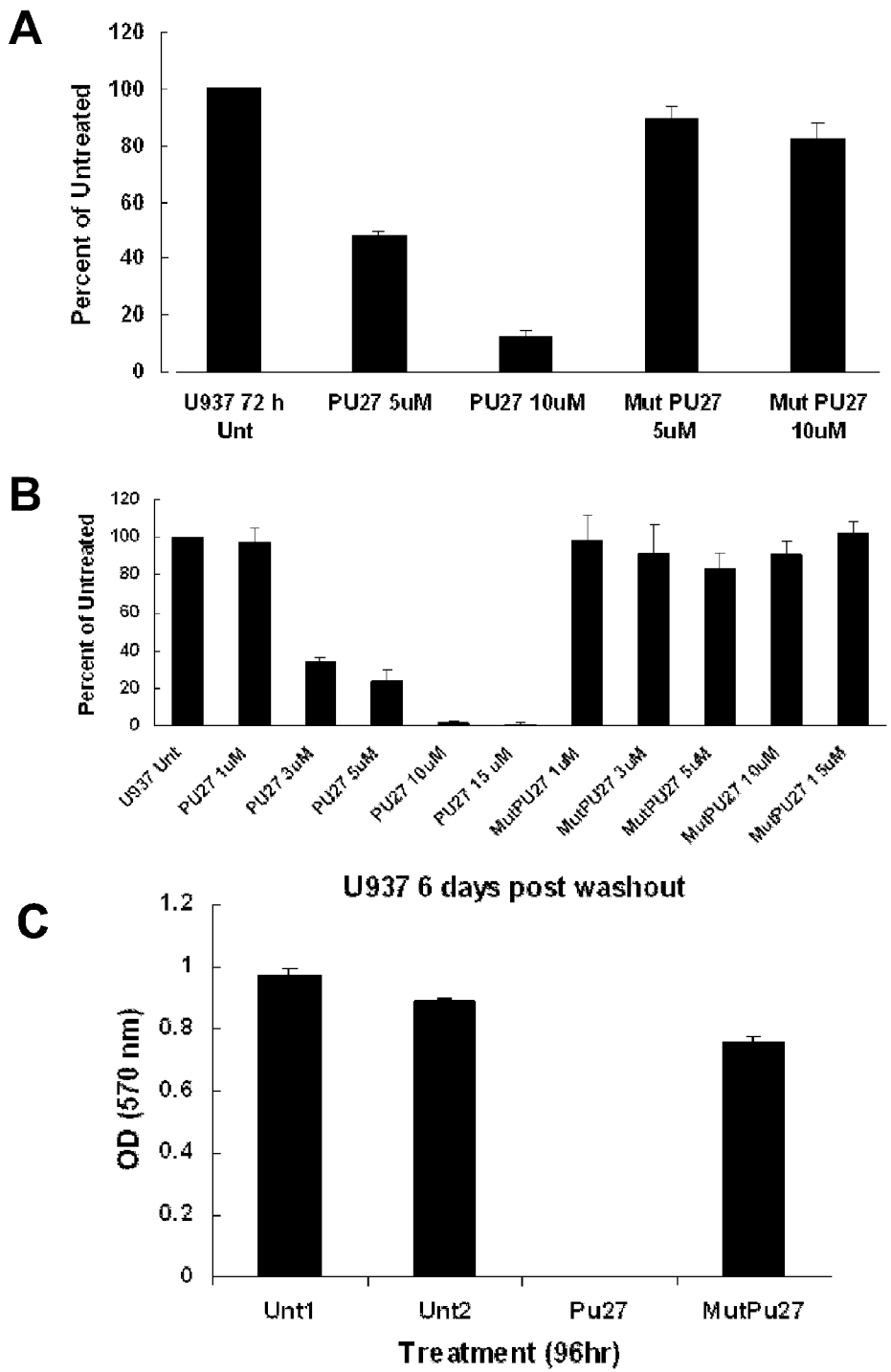
Figure 34:
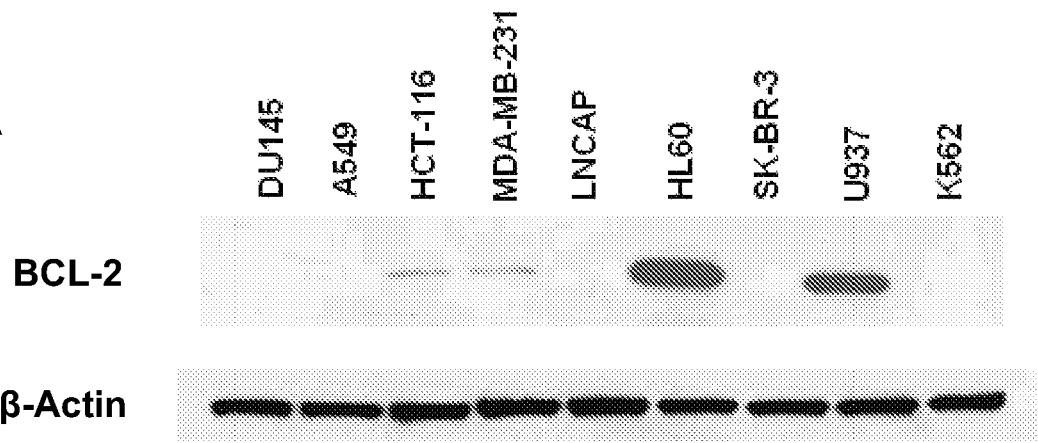
Figure 34:
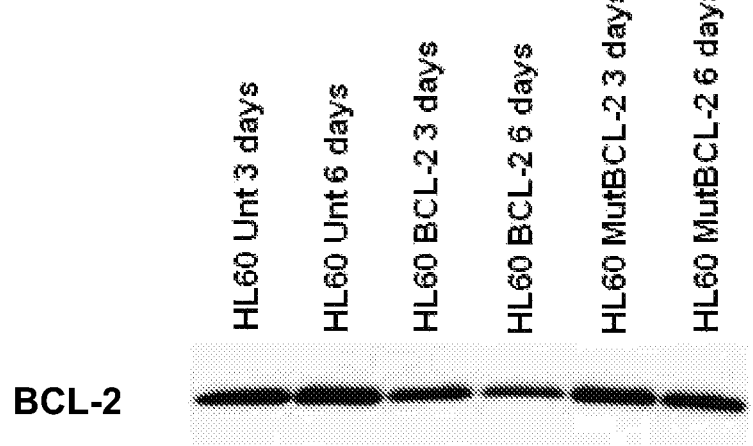

FIG. 34 (A) Basal protein expression of BCL-2 in various cancer cell lines as determined by Western blot analysis. β-actin was used as the loading control. Note high levels of BCL-2 protein expression in HL60 and U937 leukemia cell lines. Growth of both of these cell lines was greatly inhibited in response to the BCL-2 GPGO (FIGS. 7 and 21) compared to other cell lines. (B) Time course of BCL-2 expression in HL60 cells treated with the BCL-2 GPGO (10 µM) or Mut-BCL-2 by Western blot analysis. The BCL-2 GPGO significantly decreased BCL-2 protein expression compared to MutBCL-2.

The following terms are used in the present application:

The term "patient," as used herein, refers to any mammalian subject, including humans.

The term "safe and effective amount" refers to an amount of a composition high enough to significantly positively modify the symptoms and/or condition to be treated, such as by inhibiting or reducing the proliferation of, or inducing cell death (for example, by inducing apoptosis) of dysplastic, hyperproliferative, or malignant cells, but low enough to avoid serious side effects (at a reasonable risk/benefit ratio), within the scope of sound medical judgment. The safe and effective amount of oligonucleotides for use in the compositions and methods of the invention herein will vary with the particular condition being treated, the age and physical condition of the patient to be treated, the severity of the condition, the duration of the treatment, the nature of concurrent therapy, the particular oligonucleotide(s) being employed, the particular pharmaceutically-acceptable carriers utilized, and like factors within the knowledge and expertise of the attending physician.

As used herein, the term "oligonucleotide" refers to a molecule comprising two or more deoxyribonucleotides or ribonucleotides. The exact size depends on a number of factors including the specificity and binding affinity to target ligands. In referring to "bases" or "nucleotides," the terms include both deoxyribonucleic acids and ribonucleic acids.

The terms "guanosine-rich promoter gene oligonucleotide," "G-rich promoter gene oligonucleotide," or "GPGO," as used herein, refer to oligonucleotides that include the G-rich promoter sequences of the genes c-Myc, VEGF, Bcl-2, K-ras, HIF-1-α, c-Myb, RET, PDGF-A, c-Kit, and Rb, which form at least one quadruplex, and any oligonucleotide which includes a sequence having at least 80% nucleic acid sequence identity with the G-rich promoter sequence of the genes c-Myc, VEGF, Bcl-2, K-ras, HIF-1-α, c-Myb, RET, PDGF-A, c-Kit, and Rb, and which forms at least one quadruplex. Quadruplex formation may be determined by circular dichroism spectroscopy (see, for example, FIGS. 1-6). In one embodiment, a GPGO includes a sequence having at least 85%, 90%, 95%, 96%, 97%, 98%, 99%, or essentially 100% nucleic acid sequence identity with the G-rich promoter sequence of c-Myc, VEGF, Bcl-2, K-ras, HIF-1-α, c-Myb, RET, PDGF-A, c-Kit, and Rb.

The term "quadruplex," as used herein, refers to nucleic acid sequences capable of forming four-stranded conformations. These quadruplex structures are comprised of a series of quartets of hydrogen-bonded guanines, which together create a roughly cubical structure. Many cancer-related genes have quadruplex forming sequences in their G-rich promoter regions. These genes include, but are not limited to, the c-Myc, c-Myb, VEGF, RET, PDGF-A, Bcl-2, c-Kit, BCL-1, K-ras, Rb and HIF1-α genes.

"Percent (%) nucleic acid sequence identity" with respect to sequences identified herein is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 of U.S. Patent Publication, publication no. US2008/0038264. The ALIGN-2 sequence comparison computer program was authored by Genentech, Inc. and the source code shown in Table 1 of U.S. Patent Publication, publication no. US2008/0038264 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 of U.S. Patent Publication, publication no. US2008/0038264. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5 of U.S. Patent Publication, publication no. US2008/0038264, demonstrate how to calculate the % nucleic acid sequence identity of the nucleic acid sequence designated "Comparison DNA" to the nucleic acid sequence designated "PRO-DNA", wherein "PRO-DNA" represents a hypothetical nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. Further details may be found in U.S. Patent Publication, publication no. US2008/0038264.

Percent nucleic acid sequence identity may also be determined using the sequence comparison program NCBI-BLAST2 (Altschul et al., Nucleic Acids Res. 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

The term "carrier," as used herein, includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The terms "treat," "treatment," and "treating," as used herein, refer to a method of alleviating or abrogating a disease, disorder, and/or symptoms thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1-arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13. Also included in the term "growth inhibitory agent" are chemotherapeutic agents.

The terms "inhibiting cell development" or "inhibiting cell growth" refer to inhibiting growth of a cell, especially a cancer cell overexpressing any of the genes identified herein, either in vitro or in vivo. Inhibiting cell growth or cell development includes blocking cell cycle progression (at a place other than S phase), for example, G1-arrest or M-phase arrest.

The term "gene expression profile," as used herein, refers to the measurement of the activity of multiple genes at once to create a global picture of cellular function.

The term "overexpress" or "overexpressed" as used herein, refer to a gene product which is expressed at levels greater than normal endogenous expression for that gene product.

The isolated oligonucleotides of the present invention, GPGOs, are rich in guanosine and are capable of forming quadruplexes, or G-quartet structures. Specifically, the oligonucleotides of the present invention are primarily comprised of thymidine and guanosine with at least one contiguous guanosine repeat in the sequence of each oligonucleotide. The G-rich oligonucleotides are stable and can remain undegraded in serum for prolonged periods of time and retain their growth inhibiting effects.

The novel oligonucleotides of the present invention, GPGOs, can be used to inhibit the proliferation of, or induce cell death in, malignant, dysplastic and/or hyperproliferative cells. Table 1 provides the sequences of GPGOs useful in the compositions and methods of the present invention.

TABLE 1

| GPGO Sequences | | |
|---|---|---|
| SEQ ID NO: 1 | c-Myc | 5' TGGGGAGGGTGGGGAGGGTGGGGAA GG 3' |
| SEQ ID NO: 2 | c-Myb | 5' GGAGGAGGAGGTCACGGAGGAGGAG GAGAAGGAGGAGGAGGA 3' |
| SEQ ID NO: 3 | VEGF | 5' GGGGCGGGCCGGGGGCGGGG 3' |
| SEQ ID NO: 4 | K-ras | 5' AGGGCGGTGTGGGAAGAGGGAAGAG GGGGAGG 3' |
| SEQ ID NO: 5 | RET | 5' AGCGGGTAGGGGCGGGGCGGGGCGG GGGCGGTCC 3' |
| SEQ ID NO: 6 | HIF-1-α | 5' GGGGAGGGGAGAGGGGGCGGGA 3' |
| SEQ ID NO: 7 | PDGF-A | 5' GGAGGCGGGGGGGGGGGGGCGGGGG CGGGGGCGGGGAGGGGCGCGGC 3' |
| SEQ ID NO: 8 | Bcl-2 | 5' GGGCGCGGGAGGAAGGGGCG GG 3' |
| SEQ ID NO: 9 | c-Kit | 5' AGGGAGGGCGCTGGGAGGAGGG 3' |
| SEQ ID NO: 10 | RB | 5' CGGGGGGTTTTGGGCGGC 3' |

The oligonucleotides can be modified at their 3' end in order to alter a specific property of the oligonucleotide. For example, the 3'-terminus of the oligonucleotide can be modified by the addition of a propyl amine group which has been found to increase the stability of the oligonucleotide to serum nucleases. Additional example of a 3' modification is the addition of a polyethylene glycol substituent via coupling to an appropriate linker to any of the above sequences. Addition of a polyethylene glycol of different molecular weights, especially between 200 and 20,000 molecular weight, results in modifying the pharmacokinetic parameters associated with the oligonucleotides. Other modifications that are well known in the art include 3' and 5' modifications, for example, the binding of cholesterol, and backbone modifications, for example, phosphorothioate substitution and/or 2'-O-methyl RNA.

Dosage Forms and Administration

The GPGOs of the present invention can be administered to a patient or subject either alone or as part of a pharmaceutical composition. The GPGOs can be administered to patients either orally, rectally, parenterally (intravenously, intramuscularly, or subcutaneously), intracisternally, intravaginally, intraperitonally, intravesically, locally (powders, ointments, or drops), or as a buccal or nasal spray.

Compositions of the GPGOs of the present invention suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active ingredient (GPGO) is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a GPGO of the present invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

In addition, the oligonucleotides of the present invention can exist in unsolvated as well as solvated forms with pharmaceutically acceptable solvents such as water, ethanol, and the like. In general, the solvated forms are considered equivalent to the unsolvated forms for the purposes of the present invention.

The GPGOs of the present invention can be administered to a patient at dosage levels in the range of about 1.5 mg to about 150 mg per day; it is also possible to administer larger amounts, such as from about 150 mg to 1 g per day. A unit dosage form of GPGOs is an amount which would be administered as a single dose. For a normal human adult having a body weight of about 70 kilograms, a dosage in the range of about 0.2 mg to about 2.0 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art. The GPGOs of the present invention can be given in single and/or multiple dosages.

In addition, it is intended that the present invention cover GPGOs made either using standard organic synthetic techniques, including combinatorial chemistry or by biological methods, such as through metabolism.

The GPGOs of the present invention may also be used in combination with other chemotherapeutic agents to provide a synergistic or enhanced efficacy or inhibition of neoplastic cell growth. For example, the GPGOs of the present invention can be administered in combination with chemotherapeutic agents including, for example, cis-platin, mitoxantrone, etoposide, camptothecin, 5-fluorouracil, vinblastine, paclitaxel, docetaxel, mithramycin A, dexamethasone, caffeine, and other chemotherapeutic agents and/or growth inhibitory agents well known to those skilled in the art.

In one embodiment of the invention, a composition for treating a patient is provided, comprising (i) a safe and effective amount of at least one oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and (ii) a carrier, wherein the oligonucleotide forms at least one quadruplex.

In another embodiment, a composition for treating a patient is provided, comprising (i) a safe and effective amount of at least two oligonucleotides, each oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10, and (ii) a carrier, wherein each of said oligonucleotides forms at least one quadruplex.

In another embodiment, a composition for treating a patient is provided, comprising (i) a safe and effective amount of at least three oligonucleotides, each oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10, and (ii) a carrier, wherein each of said oligonucleotides forms at least one quadruplex.

In one embodiment, any of the above compositions comprises one or more sequences having at least 85%, 90%, 95%, 96%, 97%, 98%, 99%, or essentially 100% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10.

In another embodiment, any of the above compositions comprise one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

In another embodiment, any of the above compositions of the present invention further comprises a chemotherapeutic agent. Suitable chemotherapeutic agents include, but are not limited to, adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also suitable are hormonal agents that act to regulate or inhibit hormone action on tumors such as tamoxifen and onapristone.

In another embodiment, any of the above compositions of the present invention further comprises a growth inhibiting agent. Suitable growth inhibitory agents include, but are not limited to, the vincas (vincristine and vinblastine); taxol; topo II inhibitors such as doxorubicin, epirubicin, daunorubicin, etoposide, and bleomycin; DNA alkylating agents such as tamoxifen, prednisone, dacarbazine, mechlorethamine, cis-platin, methotrexate, 5-fluorouracil, and cytosine arabinoside ("Ara-C"). Also included in the term "growth inhibitory agent" are chemotherapeutic agents.

In another embodiment, a method of treating cancer is provided, comprising administering to a patient in need thereof a composition comprising (i) a safe and effective amount of at least one oligonucleotide comprising a sequence having at least 80% nucleic acid sequence identity with a sequence selected from the group consisting of SEQ ID NOS: 1-10, and combinations thereof, and (ii) a carrier, wherein the oligonucleotide forms at least one quadruplex. In another embodiment, the composition of the method comprises a safe and effective amount of two oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. In another embodiment, the composition of the method comprises a safe and effective amount of three oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. The composition of the method can be administered to the patient in a variety of modes, including but not limited to, orally, rectally, parenterally, intracisternally, intravaginally, intraperitoneally, intravesically, locally, or as a buccal or nasal spray. In a specific embodiment, the type of cancer to be treated includes, but is not limited to, leukemia, lymphoma, brain cancer, breast cancer, lung cancer, pancreatic cancer, colon cancer, ovarian cancer, liver cancer, prostate cancer, bone cancer, gastro-intestinal cancer, ocular cancer, head and neck cancer, and melanoma.

In another embodiment, a method of inhibiting cell growth is provided, comprising contacting a cell with a composition comprising (i) an effective amount or a safe and effective amount of at least one oligonucleotide comprising a sequence having at least 80% nucleic acid sequence identity with a sequence selected from the group consisting of SEQ ID NOS: 1-10, and combinations thereof, and (ii) a carrier, wherein the oligonucleotide forms at least one quadruplex. In another embodiment, the composition of the method comprises an effective amount or a safe and effective amount of two oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. In another embodiment, the composition of the method comprises an effective amount or a safe and effective amount of three oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. In one embodiment, the composition of the method may be administered in vivo, to a subject, or in vitro, to cells. In a specific embodiment, the composition is administered to a patient. The composition of the method can be administered to the patient in a variety of modes, including but not limited to, orally, rectally, parenterally, intracistemally, intravaginally, intraperitoneally, intravesically, locally, or as a buccal or nasal spray.

In a further embodiment, a method of inhibiting telomerase activity of a cell is provided, comprising contacting the cell with a composition comprising (i) an effective amount or a safe and effective amount of at least one oligonucleotide comprising a sequence having at least 80% nucleic acid sequence identity with a sequence selected from the group consisting of SEQ ID NOS: 1-10, and combinations thereof, and (ii) a carrier, wherein the oligonucleotide forms at least one quadruplex. In another embodiment, the composition of the method comprises an effective amount or a safe and effective amount of two oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. In another embodiment, the composition of the method comprises a safe and effective amount of three oligonucleotides, each oligonucleotide comprising a sequence having at least 80% nucleic acid sequence identity with a sequence selected from the group consisting of SEQ ID NOS: 1-10, wherein each of said oligonucleotides forms at least one quadruplex. In one embodiment, the composition of the method may be administered in vivo, to a subject, or in vitro, to cells. In a specific embodiment, the composition is administered to a patient. The composition of the method can be administered to the patient in a variety of modes, including but not limited to, orally, rectally, parenterally, intracistemally, intravaginally, intraperitoneally, intravesically, locally, or as a buccal or nasal spray.

In another embodiment, a method for treating a patient having a tumor is provided, the method comprising: (a) performing a biopsy of the patient's tumor; (b) determining a gene expression profile of the tumor; (c) identifying one or more genes that are overexpressed in the tumor, based on the gene expression profile of step (b); (d) selecting one or more GPGO sequences corresponding to the overexpressed genes identified in step (c); (e) administering to the patient a composition comprising a safe and effective amount of the one or more GPGO sequences of step (c). In a specific embodiment, the one or more GPGO sequences have at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and wherein each of the one or more GPGO sequences form at least one quadruplex.

EXAMPLES

The following examples are given by way of illustration and are in no way intended to limit the scope of the present invention.

Example 1

The c-myc Quadruplex Forming Sequence Inhibits c-myc Expression and Leukemic Cell Proliferation In order to determine the biological role of PU27 on cellular proliferation and c-myc expression, U937 leukemia cells were treated with 10 µM of PU27, the G-rich quadruplex forming sequence of the gene c-myc, or a 27 by mutant sequence (MutPU27), which lacks strings of two or more guanines and does not form quadruplex structures. Changes in cell proliferation were measured and compared to c-myc mRNA. Quadruplex formation was confirmed by circular dichroism spectroscopy. PU27 formed a stable parallel quadruplex structure while the MutPU27 did not form a quadruplex.

After 72 h of exposure to PU27, U937 proliferation was inhibited by more than 90% compared to untreated U937 cells, while MutPU27 treatment had only a minimal effect. Decreased proliferation with Pu27 corresponded with a 90% decrease in c-myc mRNA.

In parallel experiments, the effect of PU27 on cells which had been stably transfected with a vector in which luciferase gene expression was regulated by the c-myc promoter was tested. The luciferase activity in these cells showed marked attenuation in cells treated with PU27, but not MutPU27.

The intracellular stability of Pu27 was determined using fluorescein-labeled Pu27. These studies demonstrated remarkable intracellular stability of Pu27, with a half life of greater than nine days.

To characterize the mechanism of action of Pu27, electrophoretic mobility shift assays (EMSA) were performed with an extract from U937 cells. These results demonstrated specific protein binding to the quadruplex sequence. The results demonstrate striking growth inhibition by the wild type c-myc promoter quadruplex forming sequence, but not by the mutated sequence. They suggest that physiologic G-quadruplex formation in the c-myc promoter region modulates cell proliferation through inhibition of c-myc mRNA. Further, these results suggest that protein binding to Pu27 plays a role in regulating Pu27-mediated inhibition of c-myc mRNA.

Example 2

The MBP-1 Tumor Suppressor Binds the c-myc Promoter Quadruplex Forming Sequence

To characterize the mechanism by which PU27 controls c-myc expression, we used proteomic techniques to identify PU27-binding proteins. Two dimensional electrophoretic gels of cytosolic and nuclear extracts were blotted and screened with G-rich (quadruplex forming) and C-rich (control) oligonucleotides. It was observed that α-enolase and MBP-1 bind the G-rich quadruplex forming oligonucleotide, but not the C-rich control oligonucleotide. Using electrophoretic mobility shift assays (EMSA), it was confirmed that both α-enolase and its alternative translation product, MBP-1, bind quadruplex forming oligonucleotides.

EMSAs were used to characterize the binding of α-enolase and MBP-1 to the c-myc quadruplex-forming sequence. Both α-enolase and MBP-1 demonstrated strong binding to Pu27. An α-enolase polyclonal antibody was able to bind and "supershift" the DNA-protein complex, demonstrating specificity. The quadruplex oligonucleotide aptamer, GRO29A, competed for α-enolase and MBP-1 binding to PU27. However, a nonquadruplex-forming oligonucleotide did not compete for binding. A mutation in the PU27 sequence, which prevents quadruplex formation, abrogated binding of both α-enolase and MBP-1. MBP-1 also binds to a downstream site in the P2 promoter.

To test the biological effect of the α-enolase/MBP-1 interaction with the c-myc promoter, the effect of constitutive overexpression of each α-enolase product was examined. Although overexpression of MBP-1 in transfected cells resulted in down regulation of c-myc expression and induction of apoptosis, constitutive overexpression of α-enolase did not alter c-myc expression or the rate of cellular proliferation. These results suggest that MBP-1 down regulates c-myc expression by simultaneous binding to the P1 and P2 promoter sequences, while α-enolase binds only the P2 sequence. This suggests a very important regulatory role for α-enolase/MBP-1 in the relationship between cellular metabolism and growth regulation. Enolase/MBP-1 quadruplex-binding likely plays an important role in regulation of cellular proliferation.

Example 3

Figure 21:
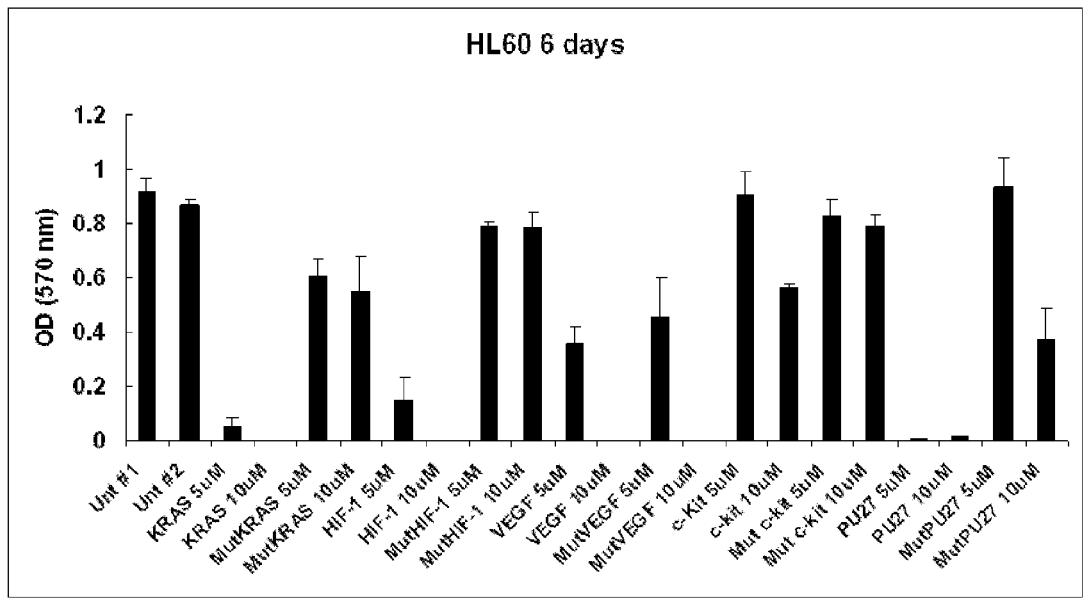
Figure 21:
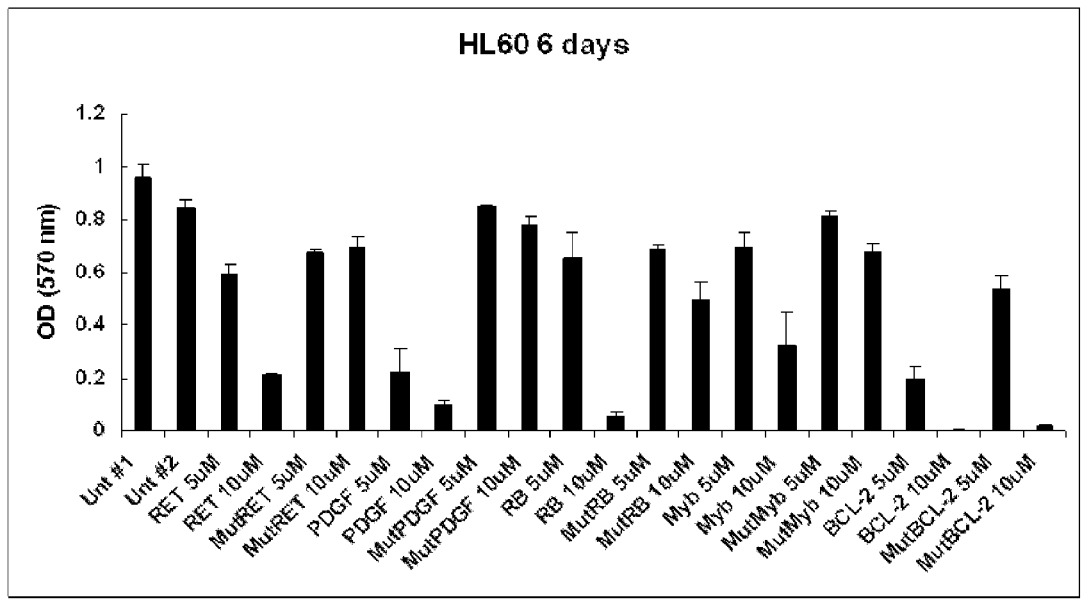

HL60 cells, a promyelocytic leukemia cell line, are treated with 5 μM and 10 μM solutions of several oligonucleotides, including GPGOs and their respective mutant sequences, the mutant sequences lacking the ability to form quadruplexes (see FIG. 21). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs KRAS (IC50≦2 μM), HIF-1-α (IC50≦2 μM), VEGF (IC50≦4 μM), PU27 (IC50≦1 μM), RET (IC50≦7 μM), PDGF (IC50≦3 μM), RB (IC50≦8 μM, Myb (IC50≦8 μM, and BCL-2 (IC50≦3 μM), as compared with their respective mutant forms.

Example 4

Figure 22:
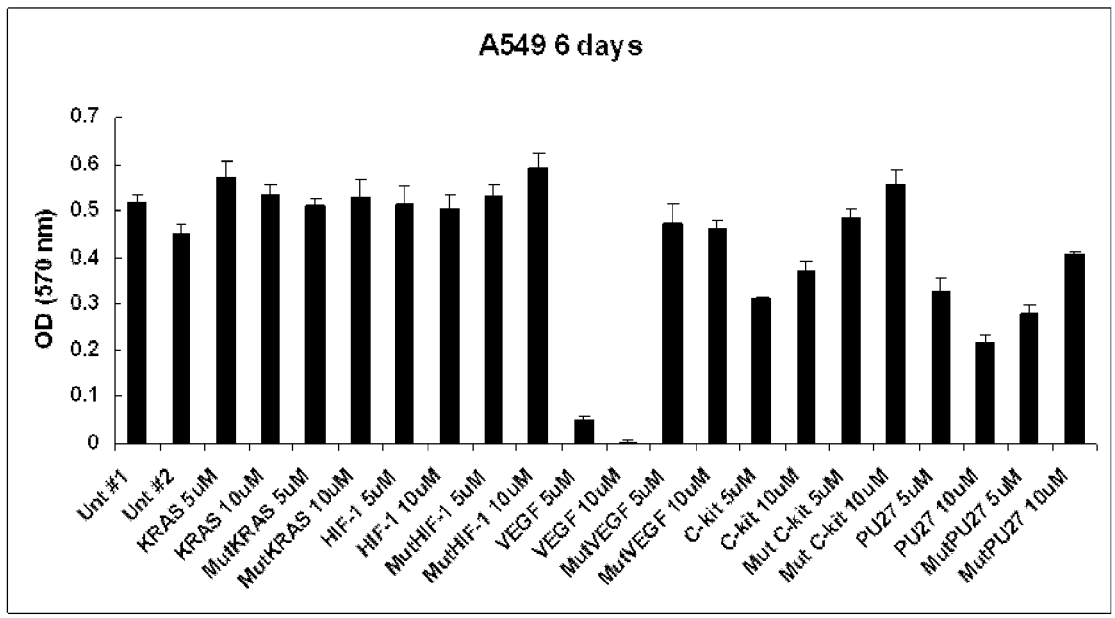
Figure 22:
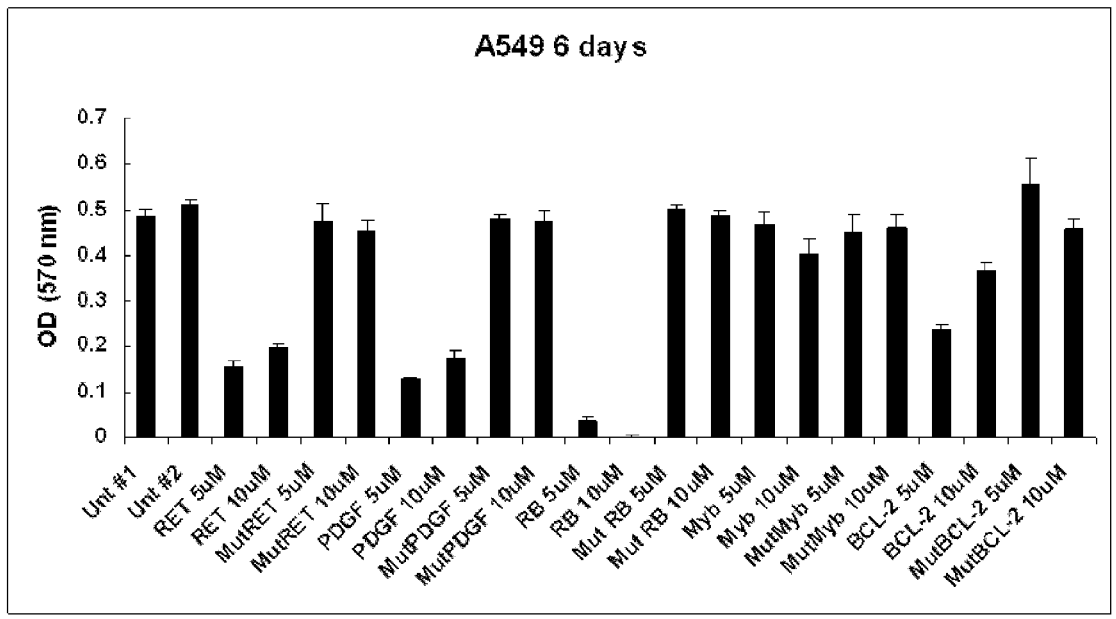

A549 cells, a lung cancer (alveolar basal epithelial) cell line, are treated with 5 μM and 10 μM solutions of several oligonucleotides, including GPGOs and their respective mutant sequences, the mutant sequences lacking the ability to form quadruplexes (see FIG. 22). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs VEGF (IC50≦2 μM), PU27 (IC50≦10 μM), RET (IC50≦3 μM), PDGF (IC50≦3 μM), RB (IC50≦2 μM), and BCL-2 (IC50≦5 μM), as compared with their respective mutant forms.

Example 5

Figure 23:
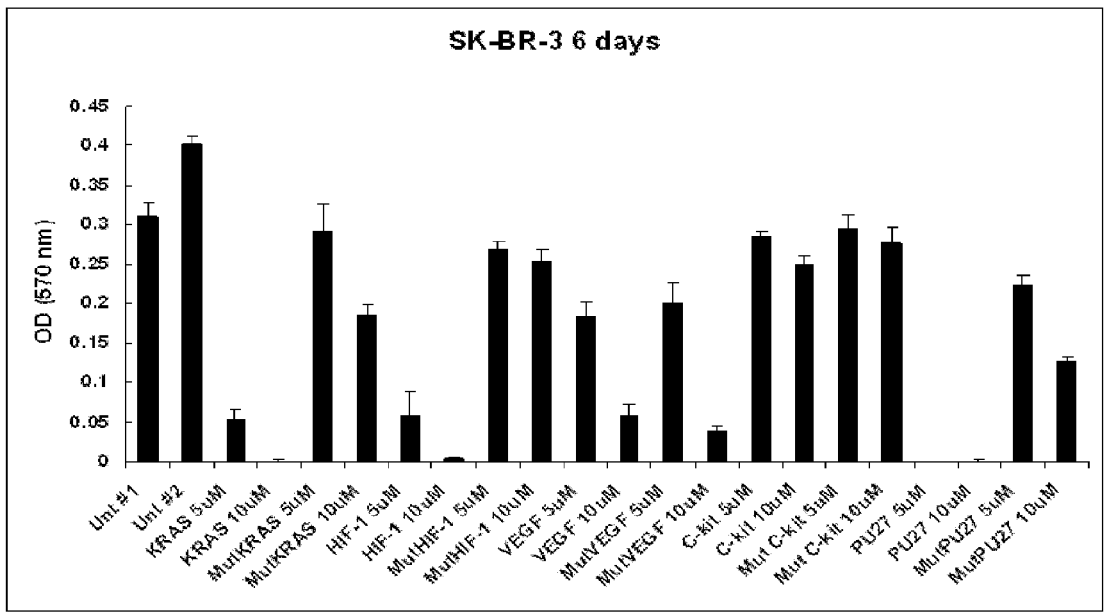
Figure 23:
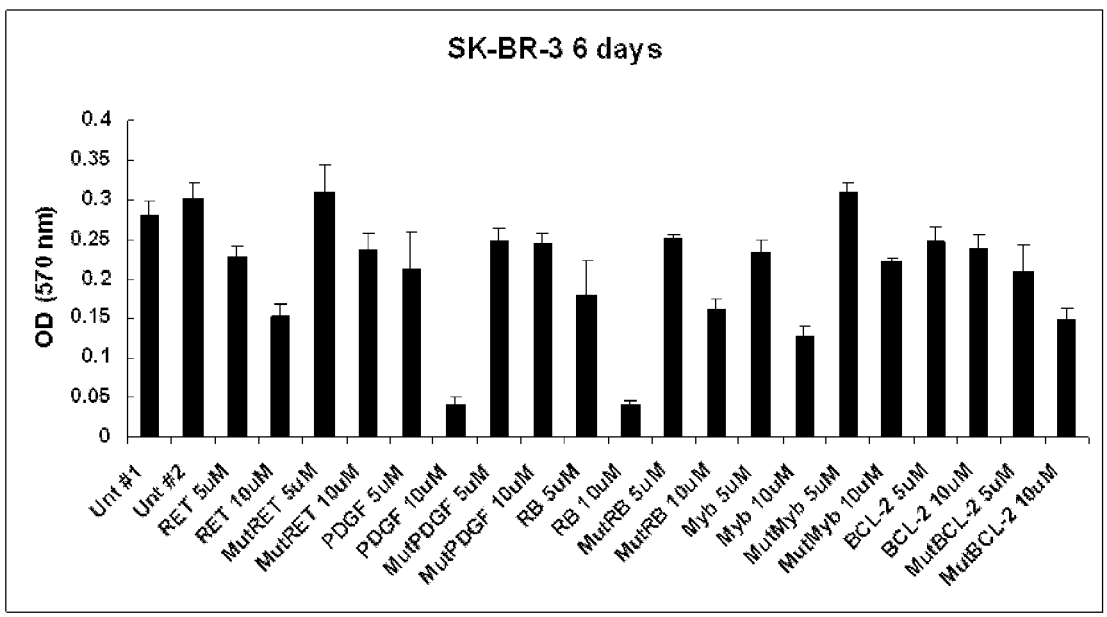

SK-BR-3 cells, a breast cancer cell line, are treated with 5 μM and 10 μM solutions of several oligonucleotides, including GPGOs and their respective mutant sequences, the mutant sequences lacking the ability to form quadruplexes (see FIG. 23). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs KRAS (IC50≦2 μM), HIF-1-α (IC50≦3 μM), VEGF (IC50≦7 μM), PU27 (IC50≦1 μM), RET (IC50≦10 μM), PDGF (IC50≦7 μM), RB (IC50≦7 μM), and Myb (IC50≦10 μM), as compared with their respective mutant forms.

Example 6

Figure 24:
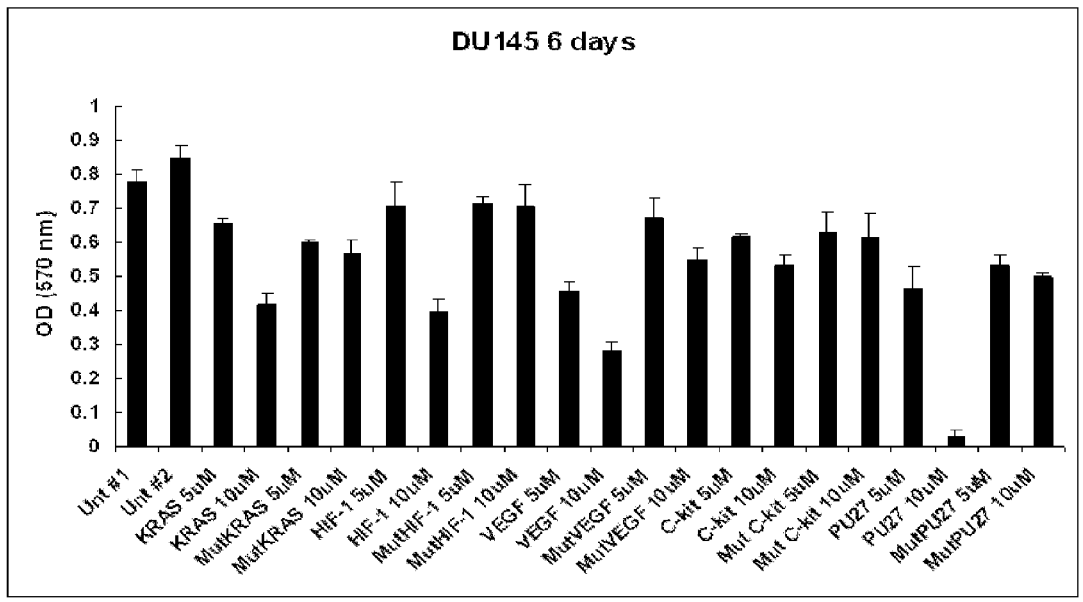
Figure 24:
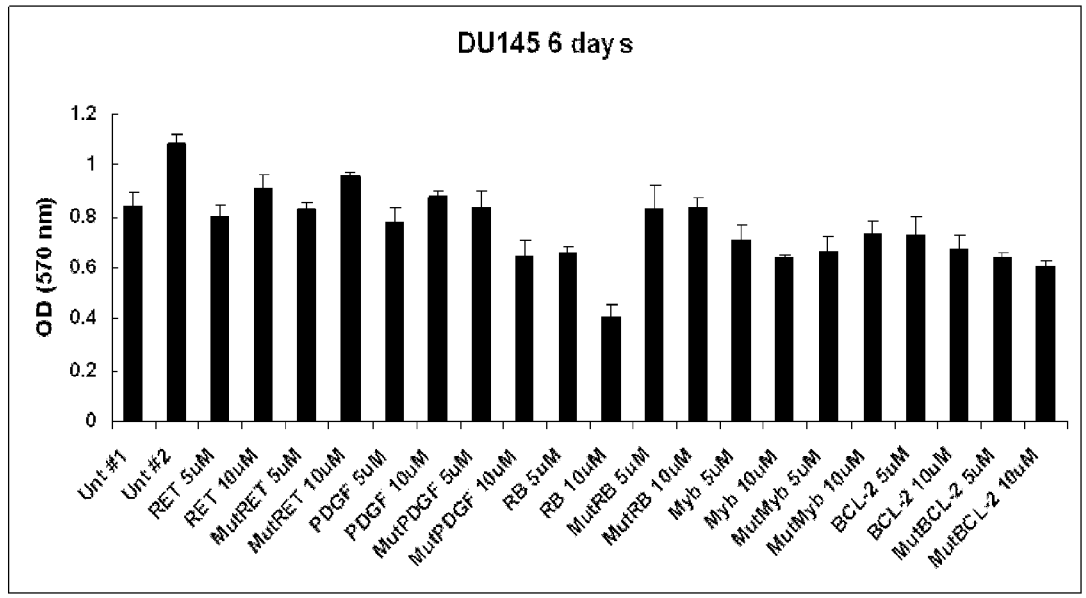

DU145 cells, a prostate cancer cell line, are treated with 5 μM and 10 μM solutions of several oligonucleotides, including GPGOs and their respective mutant sequences, the mutant sequences lacking the ability to form quadruplexes (see FIG. 24). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs KRAS (IC50≦10 μM), HIF-1-α (IC50≦10 μM), VEGF (IC50≦8 μM), PU27 (IC50≦6 μM), and RB (IC50≦9 μM), as compared with their respective mutant forms.

Example 7

Figure 25:
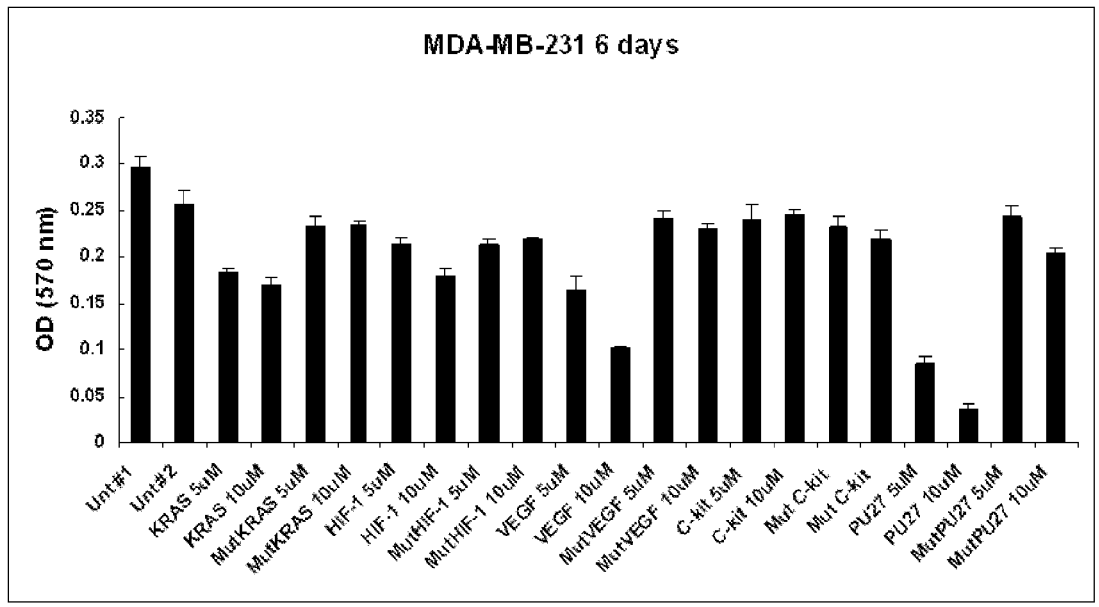
Figure 25:
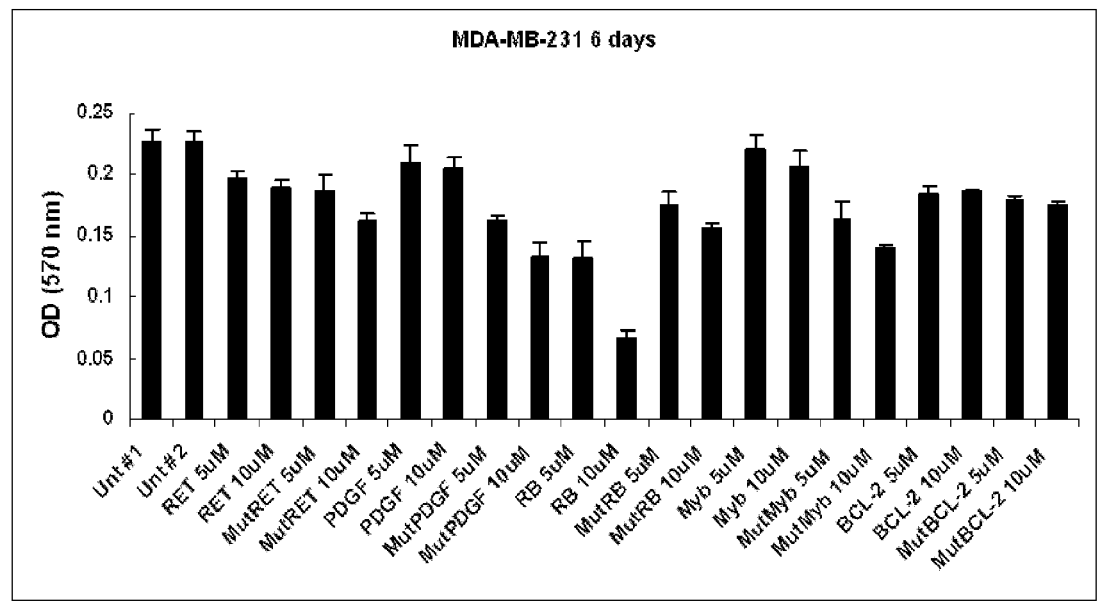

MDA-MB-231 cells, a breast cancer cell line, are treated with 5 μM and 10 μM solutions of several oligonucleotides, including GPGOs and their respective mutant sequences, the mutant sequences lacking the ability to form quadruplexes (see FIG. 25). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs VEGF (IC50≦8 μM), PU27 (IC50≦3 μM), and RB (IC50≦7 μM), as compared with their respective mutant forms.

Example 8

Figure 26:
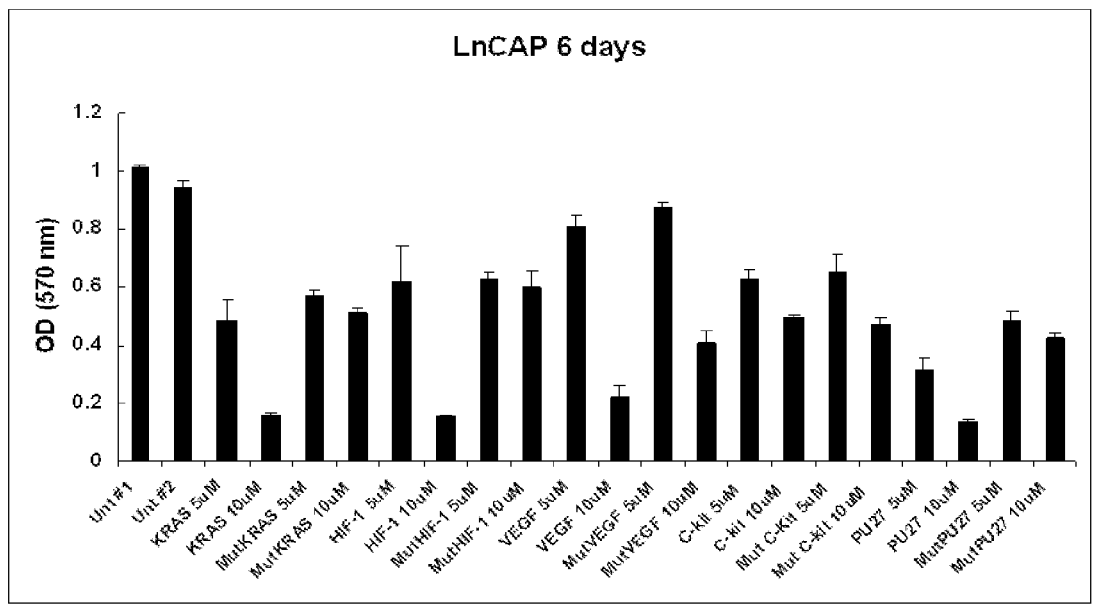
Figure 26:
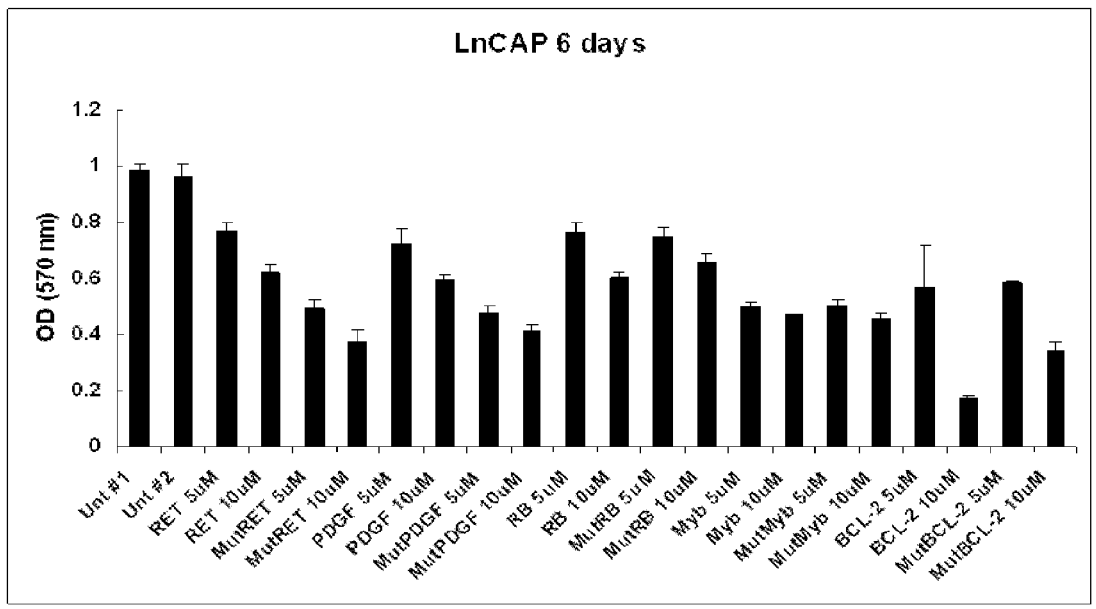

LnCAP cells, a prostate cancer cell line, are treated with 5 μM and 10 μM solutions of several oligonucleotides, including GPGOs and their respective mutant sequences, the mutant sequences lacking the ability to form quadruplexes (see FIG. 26).

Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGOs KRAS (IC50≦5 μM), HIF-1-α (IC50≦6 μM), VEGF (IC50≦7 μM), c-KIT (IC50≦10 μM), PU27 (IC50≦3 μM), Myb IC50≦10 μM), and BCL-2 (IC50≦6 μM), as compared with their respective mutant forms.

Example 9

Figure 27:
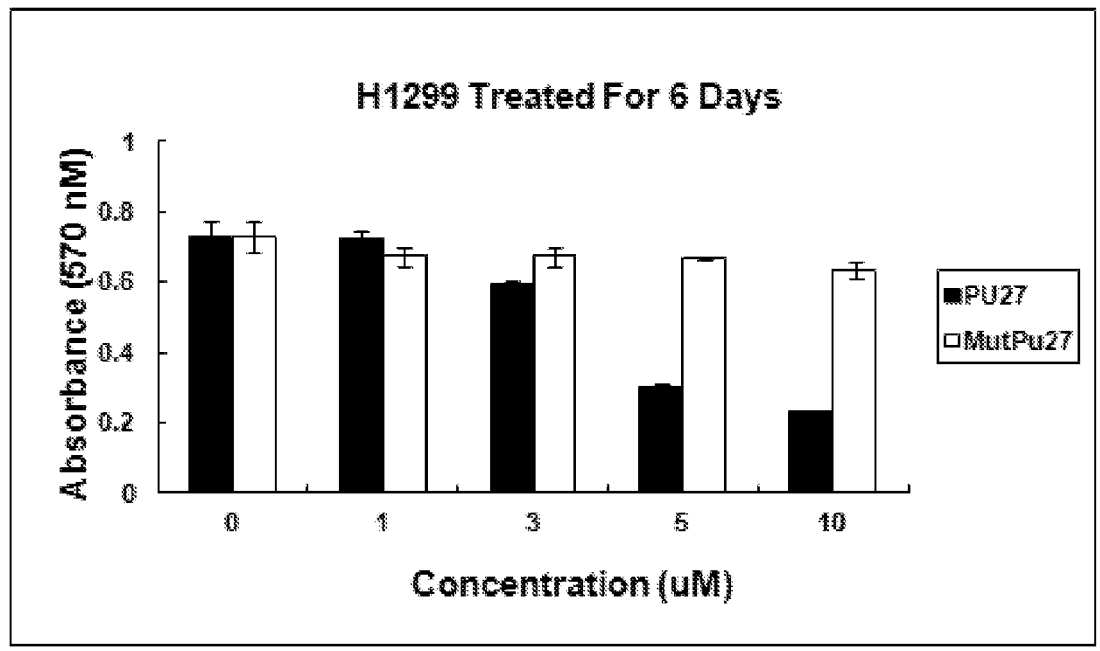
Figure 27:
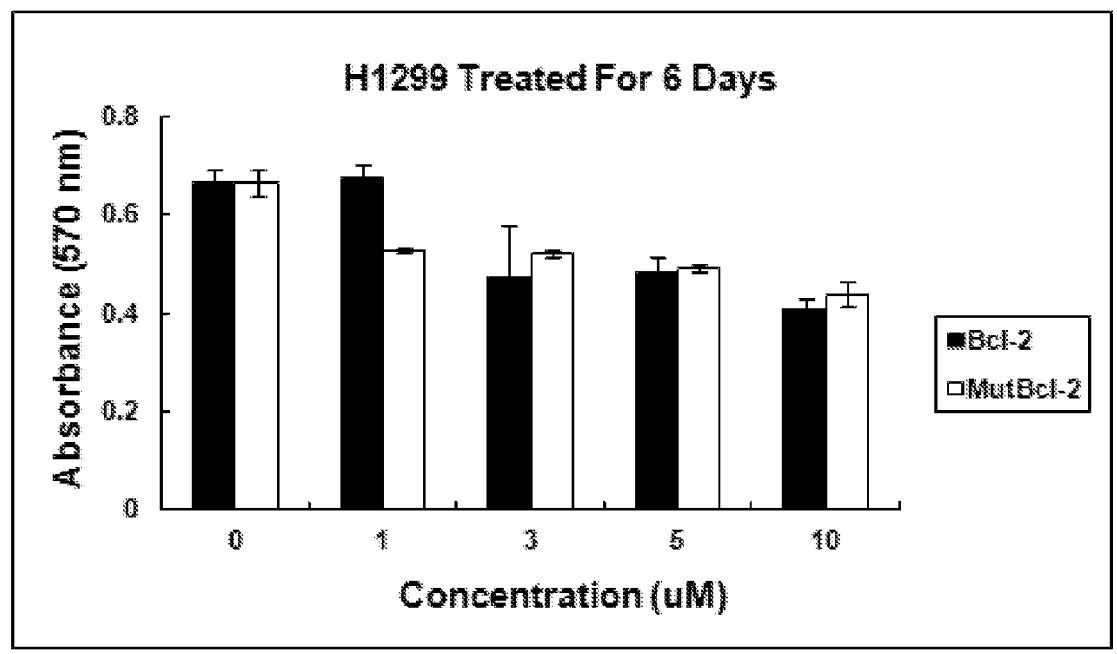

H1299 cells, a lung cancer cell line, are treated with 5 μM and 10 μM solutions of several oligonucleotides, including GPGOs and their respective mutant sequences, the mutant sequences lacking the ability to form quadruplexes (see FIG. 27). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutPDGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGO PU27 (IC50≦5 μM), as compared with the respective mutant form.

Example 10

Figure 28:
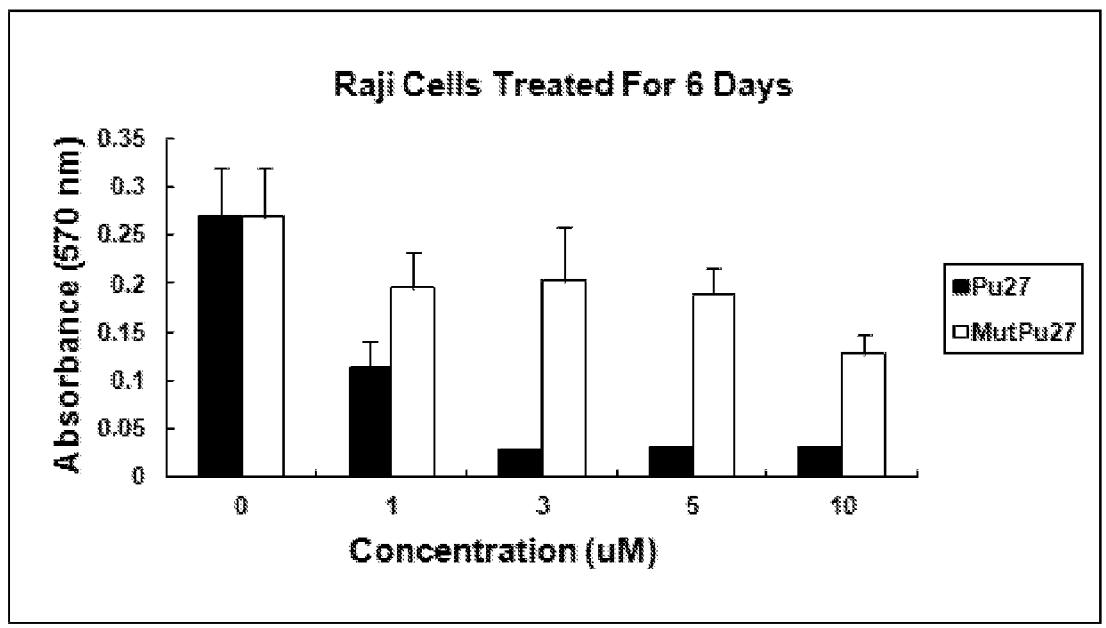
Figure 28:
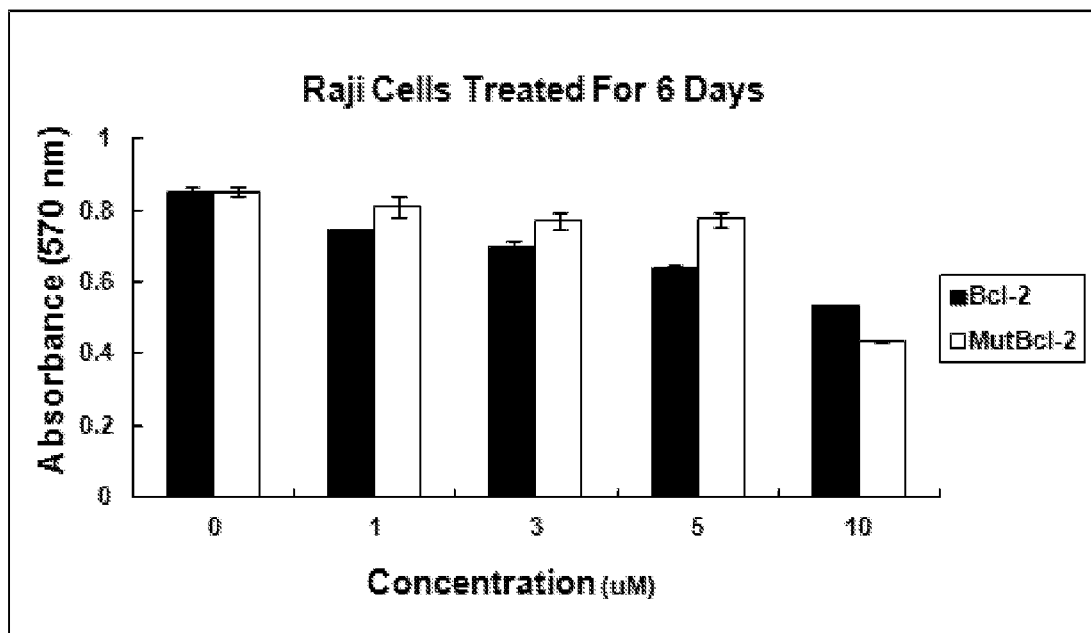

Raji cells, a Burkitt's lymphoma cell line, are treated with 5 μM and 10 μM solutions of several oligonucleotides, including GPGOs and their respective mutant sequences, the mutant sequences lacking the ability to form quadruplexes (see FIG. 28). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutP-DGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGO PU27 (IC50≦0.8 µM), as compared with the respective mutant form.

Example 11

Figure 29:
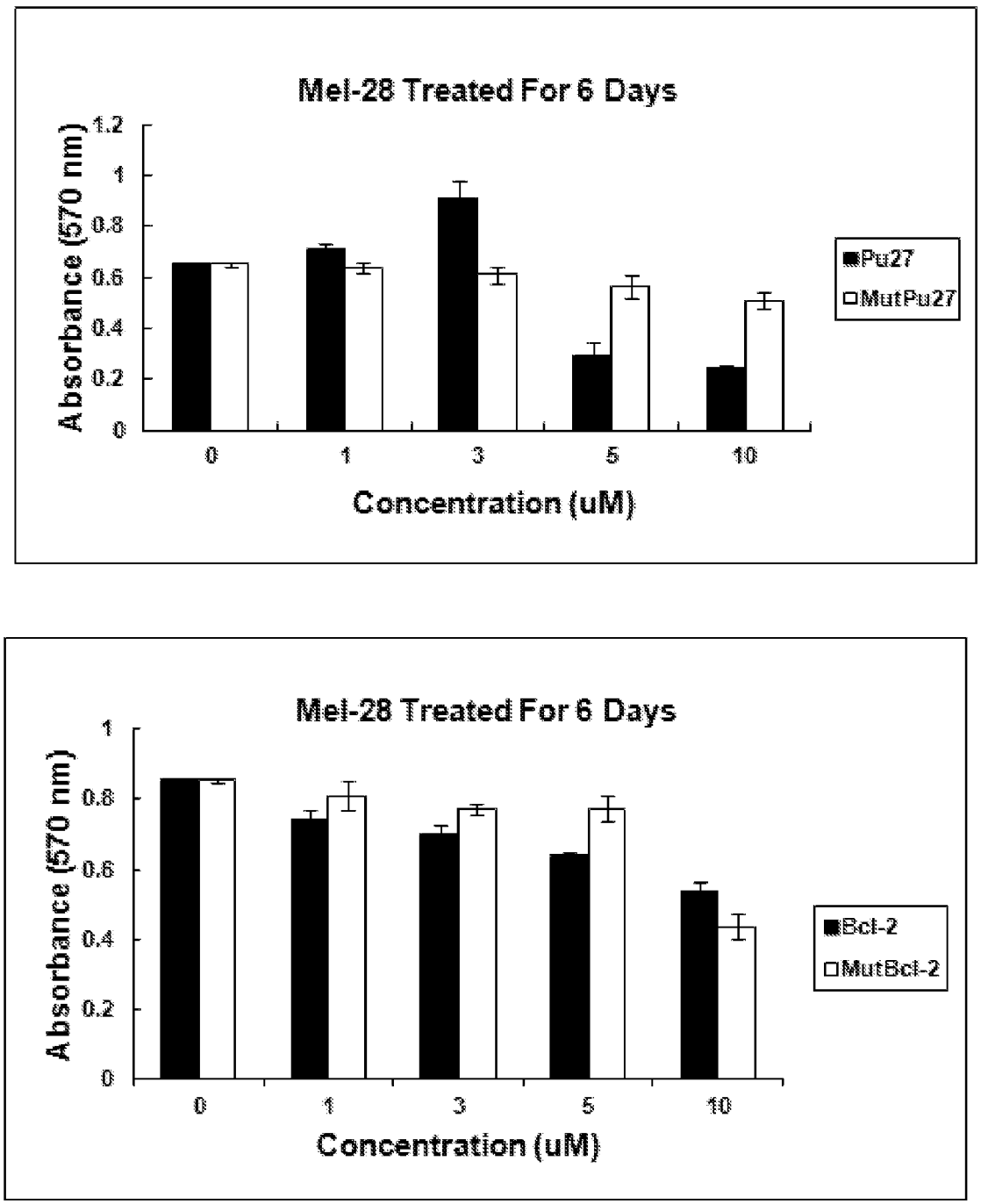
Figure 30:
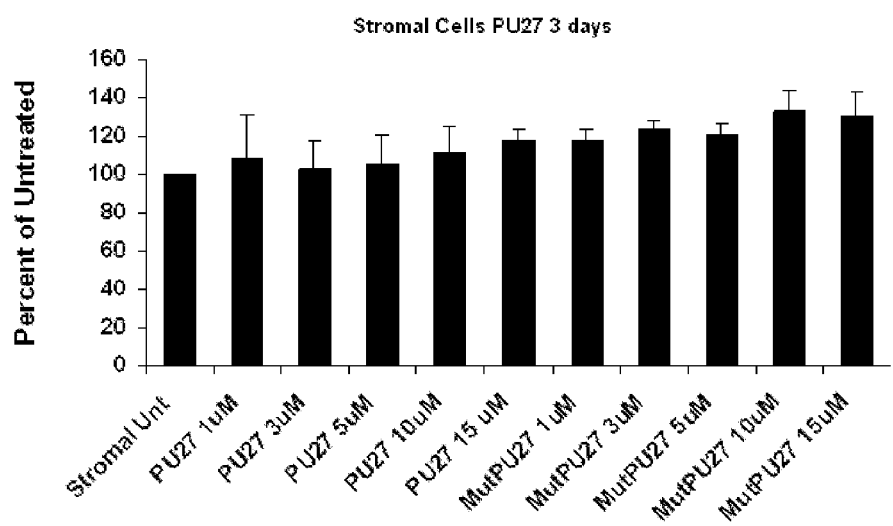
FIG. 30 shows results in cell proliferation of non-cancerous stromal cells in response to PU27 after 3 days (A) and 6 days (B). Treatment of stromal cells up to 15 µM had not affect on stromal cell proliferation suggesting GPGOs only inhibit proliferation of cancer cells.
Figure 30:
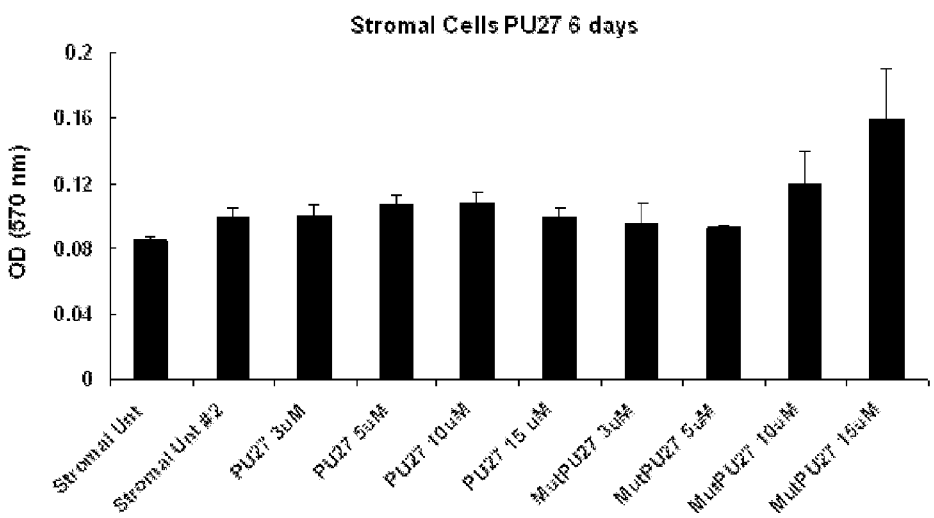
Figure 31:
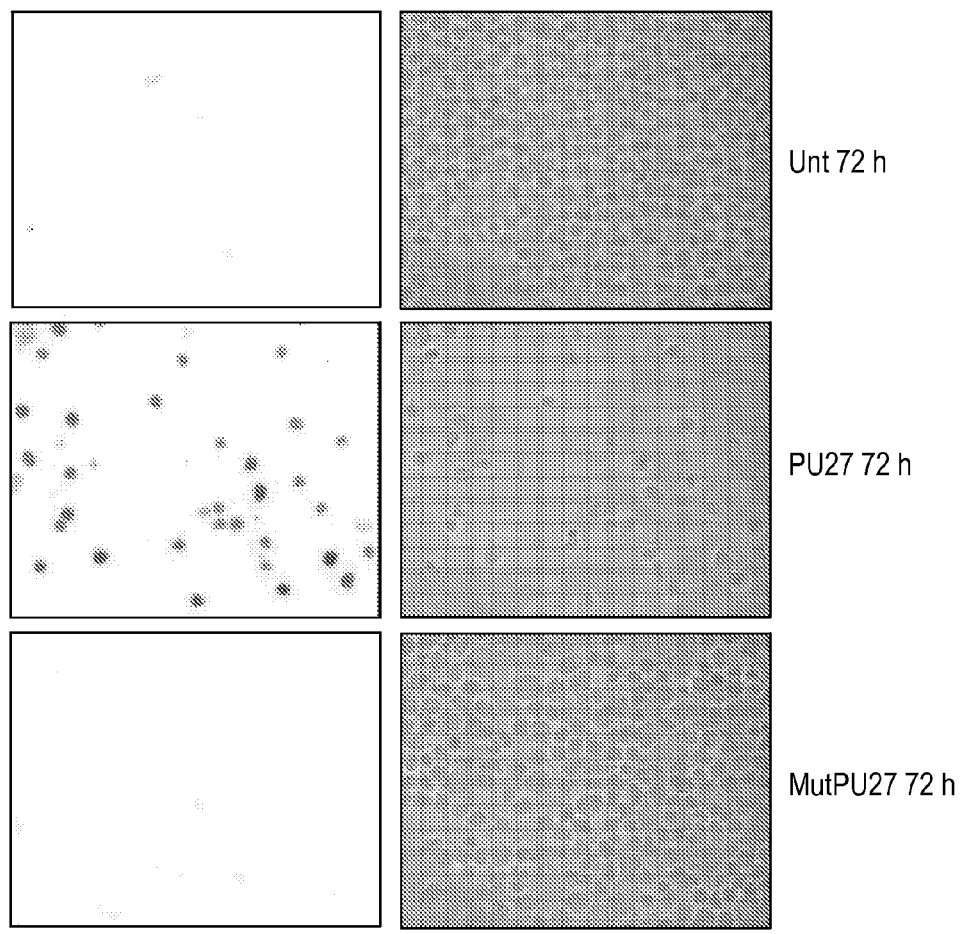
FIG. 31 shows an increase in DNA fragmentation (green) in U937 by TUNEL staining after 72 h treatment with 10 µM PU27 compared to untreated cells (Unt) and cells treated with MutPU27 (10 µM).

Mel-28 cells, a melanoma cell line, are treated with 5 µM and 10 µM solutions of several oligonucleotides, including GPGOs and their respective mutant sequences, the mutant sequences lacking the ability to form quadruplexes (see FIG. 29). Test oligonucleotides include (A) KRAS, MutKRAS, HIF-1-α, MutHIF-1-α, VEGF, MutVEGF, c-KIT, Mut c-KIT, PU27, and MutPU27; and (B) RET, MutRET, PDGF, MutP-DGF, RB, MutRB, Myb, MutMyb, BCL-2, and MutBCL-2. After 6 days, cell proliferation is assessed via MTT assay. Results indicate cell proliferation is inhibited by ≧50% by treatment with the GPGO PU27 (IC50≦5 µM), as compared with the respective mutant form.

Example 12

HL60 cells, a promyelocytic leukemia cell line, are treated with solutions of several combinations of oligonucleotides. The test combinations include KRAS/HIF-1-α, KRAS/PU27, PU27/HIF-1-α, PU27/BCL-2, and KRAS/HIF-1-α/PU27. Using untreated and individual sequences as controls, cell proliferation is measured 3 days after addition of 0.2, 1, 5, and 10 µM solutions of these GPGOs mixtures. A significant inhibition of cell proliferation is observed when combinations of sequences are used, as compared to the individual sequences. Further, higher inhibition is observed at the lower concentrations of the GPGOs combinations as compared to the individuals GPGOs.

Example 13

K562 cells, a leukemia cell line, are treated with solutions of several combinations of oligonucleotides. The test combinations include PU27/BCL-2, PU27/KRAS, and KRAS/BCL-2. Using untreated and individual sequences as controls, cell proliferation is measured 3 days after addition of 0.2, 1, 5, and 10 µM solutions of these GPGOs mixtures. A significant inhibition of cell proliferation is observed when combinations of sequences are used, as compared to the individual sequences. The results indicate an additive or potentially synergistic effect when sequences are combined.

Example 14

LnCap cells, a human adenocarcinoma prostate cell line, are treated with solutions of several combinations of oligonucleotides. The test combinations include PU27/KRAS and KRAS/HIF-1-α GPGO sequences at 0.2, 1, 5, and 10 µM. A modest increase in the inhibition of cancer cell proliferation is seen for both combinations after 6 days as compared to the individual sequences.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A composition for treating a patient, comprising:
   (i) a safe and effective amount of at least one isolated oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and
   (ii) a carrier,
   wherein the isolated oligonucleotide forms at least one quadruplex.

2. The composition of claim 1, comprising at least two isolated oligonucleotides, each oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10 wherein each of said isolated oligonucleotides forms at least one quadruplex.

3. The composition of claim 1, comprising at least three isolated oligonucleotides, each oligonucleotide comprising a sequence having at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO:10 wherein each of said isolated oligonucleotides forms at least one quadruplex.

4. The composition of claim 1, wherein the isolated oligonucleotide comprises a sequence having at least 90% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

5. The composition of claim 1, wherein the isolated oligonucleotide comprises a sequence having at least 95% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

6. The composition of claim 1, wherein the isolated oligonucleotide comprises a sequence having at least 98% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

7. The composition of claim 1, wherein the isolated oligonucleotide comprises a sequence having at least 99% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

8. The composition of claim 1, wherein the isolated oligonucleotide comprises a sequence having essentially 100% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

9. The composition of claim 1, wherein the isolated oligonucleotide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof.

10. The composition of claim 1, further comprising a growth inhibiting agent.

11. The composition of claim 1, further comprising a chemotherapeutic agent.

12. A method of treating cancer comprising administering to a patient in need thereof the composition of claim 1.

13. A method of inhibiting cell growth, comprising contacting a cell with the composition of claim 1.

14. A method of inhibiting telomerase activity of a cell, comprising contacting the cell with the composition of claim 1.

15. The method of claim 12 wherein the composition is administered to a patient orally, rectally, parenterally, intracisternally, intravaginally, intraperitoneally, intravesically, locally, or as a buccal or nasal spray.

16. The method of claim 12 wherein the cancer is selected from the group consisting of leukemia, lymphoma, brain cancer, breast cancer, lung cancer, pancreatic cancer, colon cancer, ovarian cancer, liver cancer, prostate cancer, bone cancer, gastro-intestinal cancer, ocular cancer, head and neck cancer, and melanoma.

17. A method of treating a patient having a tumor, the method comprising:
(a) performing a biopsy of the patient's tumor;
(b) determining a gene expression profile of the tumor;
(c) identifying one or more genes that are overexpressed in the tumor, based on the gene expression profile of step (b);
(d) selecting one or more guanosine-rich promoter gene oligonucleotide (GPGO) sequences corresponding to the overexpressed genes identified in step (c);
(e) administering to the patient a composition comprising a safe and effective amount of the one or more GPGO sequences of step (d), wherein the one or more GPGO sequences have at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and combinations thereof, and wherein each of the one or more GPGO sequences forms at least one quadruplex.

18. The method of claim 17, wherein the one or more GPGO sequences are selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, and combinations thereof, and wherein each of the one or more GPGO sequences forms at least one quadruplex.

* * * * *